US010682368B2

(12) United States Patent
Perron et al.

(10) Patent No.: US 10,682,368 B2
(45) Date of Patent: Jun. 16, 2020

(54) METHODS OF TREATING FELINE CORONAVIRUS INFECTIONS

(71) Applicants: Gilead Sciences, Inc., Foster City, CA (US); The Regents of the University of Calfornia, Oakland, CA (US)

(72) Inventors: Michel Joseph Perron, Morgan Hill, CA (US); Niels C. Pedersen, Oakland, CA (US)

(73) Assignees: GILEAD SCIENCES, INC., Foster City, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/919,750

(22) Filed: Mar. 13, 2018

(65) Prior Publication Data

US 2018/0296584 A1 Oct. 18, 2018

Related U.S. Application Data

(60) Provisional application No. 62/470,944, filed on Mar. 14, 2017.

(51) Int. Cl.
| A61K 31/706 | (2006.01) |
| A61K 31/12 | (2006.01) |
| A61K 31/14 | (2006.01) |
| A61P 31/12 | (2006.01) |
| A61P 31/14 | (2006.01) |

(52) U.S. Cl.
CPC ............ A61K 31/706 (2013.01); A61P 31/12 (2018.01); A61P 31/14 (2018.01)

(58) Field of Classification Search
CPC ......... A61K 31/706; A61P 31/14; A61P 31/12
See application file for complete search history.

(56) References Cited

U.S. PATENT DOCUMENTS

| 4,816,570 | A | 3/1989 | Farquhar |
| 4,968,788 | A | 11/1990 | Farquhar |
| 5,663,159 | A | 9/1997 | Starrett, Jr. et al. |
| 5,792,756 | A | 8/1998 | Starrett, Jr. et al. |
| 6,312,662 | B1 | 11/2001 | Erion et al. |
| 6,476,030 | B1 | 11/2002 | Carling et al. |
| 6,656,915 | B1 | 12/2003 | Bantia et al. |
| 6,909,011 | B2 | 6/2005 | Skranc et al. |
| 7,105,493 | B2 | 9/2006 | Sommadossi et al. |
| 7,125,855 | B2 | 10/2006 | Bhat et al. |
| 7,176,203 | B2 | 2/2007 | Chambers et al. |
| 7,268,119 | B2 | 9/2007 | Cook et al. |
| 7,285,658 | B2 | 10/2007 | Cook et al. |
| 7,368,437 | B1 | 5/2008 | Bojack et al. |
| 7,390,791 | B2 | 6/2008 | Becker et al. |
| 7,429,571 | B2 | 9/2008 | Chand et al. |
| 7,514,410 | B2 | 4/2009 | Babu et al. |
| 7,560,434 | B2 | 7/2009 | Babu et al. |
| 7,598,230 | B2 | 10/2009 | Cook et al. |
| 7,608,597 | B2 | 10/2009 | Sommadossi et al. |
| 7,713,941 | B2 | 5/2010 | Cook et al. |
| 7,807,653 | B2 | 10/2010 | Cook et al. |
| 7,842,672 | B2 | 11/2010 | Boojamra et al. |
| 7,973,013 | B2 | 7/2011 | Cho et al. |
| 7,994,139 | B2 | 8/2011 | Babu et al. |
| 8,008,264 | B2 | 8/2011 | Butler et al. |
| 8,012,941 | B2 | 9/2011 | Cho et al. |
| 8,012,942 | B2 | 9/2011 | Butler et al. |
| 8,071,568 | B2 | 12/2011 | Narjes et al. |
| 8,119,607 | B2 | 2/2012 | Francom et al. |
| 8,242,085 | B2 | 8/2012 | Babu et al. |
| 8,318,682 | B2 * | 11/2012 | Butler .................... C07H 19/23 514/23 |
| 8,415,308 | B2 | 4/2013 | Cho et al. |
| 8,455,451 | B2 * | 6/2013 | Cho ........................ A61K 31/41 514/23 |
| 8,853,171 | B2 * | 10/2014 | Butler .................. C07D 487/04 514/23 |
| 8,871,737 | B2 | 10/2014 | Smith et al. |
| 8,889,159 | B2 | 11/2014 | Clearly et al. |
| 8,980,865 | B2 | 3/2015 | Wang |
| 9,090,642 | B2 | 7/2015 | Cho et al. |
| 9,243,022 | B2 | 1/2016 | Beigelman et al. |
| 9,249,174 | B2 | 2/2016 | Beigelman et al. |
| 9,278,990 | B2 | 3/2016 | Smith et al. |
| 9,388,208 | B2 * | 7/2016 | Clarke .................... C07H 7/06 |

(Continued)

FOREIGN PATENT DOCUMENTS

| JP | 4107629 B | 10/1966 |
| WO | WO1991019721 A1 | 12/1991 |

(Continued)

OTHER PUBLICATIONS

European Patent Office, International Search Report and Written Opinion for PCT International Application No. PCT/US2018/022166, dated Jun. 11, 2018, 18 pages.

Clarke, et al., Discovery of [beta]-d-2'-deoxy-2'-[alpha]-fluoro-4'[alpha]-cyano-5-aza-7,9-dideaza adenosine as a potent nucleoside inhibitor of respiratory syncytial virus with excellent selectivity over mitochondrial, BioOrganic & Medicinal Chemistry Letters, Apr. 29, 2015, pp. 2484-2487, vol. 25, No. 12.

(Continued)

Primary Examiner — Lawrence E Crane

(74) Attorney, Agent, or Firm — Mintz, Levin, Cohn, Ferris, Glovsky and Popeo, P.C.

(57) ABSTRACT

Provided are methods of treating feline Coronavirus infections using carbanucleoside compounds having a 1'-(4-aminopyrrolo[2,1-f][1,2,4]triazin-7-yl) substituent, or a pharmaceutically acceptable salt thereof. An exemplary compound is (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile.

18 Claims, 8 Drawing Sheets

(56) References Cited

U.S. PATENT DOCUMENTS

| | | |
|---|---|---|
| 9,393,256 B2 | 7/2016 | Ray et al. |
| 9,481,703 B2 | 11/2016 | Kalayanov et al. |
| 9,487,544 B2 | 11/2016 | Cho et al. |
| 9,540,411 B2 | 1/2017 | Kalayanov et al. |
| 9,542,154 B2 | 1/2017 | Rubanovich et al. |
| 9,549,941 B2 | 1/2017 | Cleary et al. |
| 9,605,018 B2 | 3/2017 | Wang et al. |
| 9,701,682 B2 | 7/2017 | Clarke et al. |
| 9,724,360 B2 | 8/2017 | Chun et al. |
| 9,828,408 B2 | 11/2017 | Kalayanov |
| 9,949,994 B2 | 4/2018 | Chun et al. |
| 10,023,600 B2 | 7/2018 | Butler et al. |
| 10,034,893 B2 * | 7/2018 | Luly ................. A61K 31/13 |
| 10,059,716 B2 * | 8/2018 | Clarke ................ A61P 31/16 |
| 10,065,958 B2 * | 9/2018 | Mackman .......... A61K 45/06 |
| 10,251,898 B2 | 4/2019 | Chun et al. |
| 10,251,904 B2 * | 4/2019 | Clarke ............. A61K 31/706 |
| 2003/0050229 A1 | 3/2003 | Sommadossi et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | McGuigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0203015 A1 | 8/2010 | Butler et al. |
| 2010/0234584 A1 | 9/2010 | Chang |
| 2010/0291031 A2 | 11/2010 | Francom et al. |
| 2010/0298257 A1 | 11/2010 | Ross et al. |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Butler et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 1/2014 | Luly et al. |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2016/0058779 A1 | 3/2016 | Casola et al. |

FOREIGN PATENT DOCUMENTS

| | | |
|---|---|---|
| WO | WO199945029 | 9/1999 |
| WO | WO2000056734 A | 9/2000 |
| WO | WO2001032153 A2 | 5/2001 |
| WO | WO2001060315 A2 | 8/2001 |
| WO | WO2001090121 A2 | 11/2001 |
| WO | WO200208241 A | 1/2002 |
| WO | WO2002008241 A2 | 1/2002 |
| WO | WO2002018404 A2 | 3/2002 |
| WO | WO2002032920 A2 | 4/2002 |
| WO | WO2002057287 A2 | 7/2002 |
| WO | WO2002057425 A2 | 7/2002 |
| WO | WO2003093272 A1 | 11/2003 |
| WO | WO2003093273 A1 | 11/2003 |
| WO | WO2003100009 A2 | 12/2003 |
| WO | WO2004046331 A | 6/2004 |
| WO | WO2005009418 A2 | 2/2005 |
| WO | WO2005123087 A | 12/2005 |
| WO | WO2006031725 A2 | 3/2006 |
| WO | WO2006050161 A2 | 5/2006 |
| WO | WO2006064033 A2 | 6/2006 |
| WO | WO2006065335 A2 | 6/2006 |
| WO | WO2006121820 A2 | 11/2006 |
| WO | WO2007027248 A2 | 3/2007 |
| WO | WO2007056170 A | 5/2007 |
| WO | WO2007064883 A1 | 6/2007 |
| WO | WO2007064931 A2 | 6/2007 |
| WO | WO2007065289 A2 | 6/2007 |
| WO | WO2007065829 A2 | 6/2007 |
| WO | WO2007097991 A2 | 8/2007 |
| WO | WO2007135134 A2 | 11/2007 |
| WO | WO2008005542 A1 | 1/2008 |
| WO | WO2008055870 A2 | 5/2008 |
| WO | WO2008079206 A | 7/2008 |
| WO | WO2008082601 A1 | 7/2008 |
| WO | WO2008085508 A2 | 7/2008 |
| WO | WO2008089105 A | 7/2008 |
| WO | WO2008116064 A1 | 9/2008 |
| WO | WO2008121634 A | 10/2008 |
| WO | WO2008141079 A1 | 11/2008 |
| WO | WO2009009951 A2 | 1/2009 |
| WO | WO2009131926 A2 | 10/2009 |
| WO | WO2009132123 A2 | 10/2009 |
| WO | WO2009132135 A2 | 10/2009 |
| WO | WO2010002877 A2 | 1/2010 |
| WO | WO2010036407 A1 | 4/2010 |
| WO | WO2010093608 A1 | 8/2010 |
| WO | WO2010099458 C | 9/2010 |
| WO | WO2010135569 A1 | 11/2010 |
| WO | WO2011011303 A1 | 1/2011 |
| WO | WO2010111381 A1 | 3/2011 |
| WO | WO2011035231 A | 3/2011 |
| WO | WO2011035250 A2 | 3/2011 |
| WO | WO2011123645 A2 | 10/2011 |
| WO | WO2011123672 A1 | 10/2011 |
| WO | WO2011150288 A1 | 12/2011 |
| WO | 2012/012776 A1 | 1/2012 |
| WO | WO2012012465 A1 | 1/2012 |
| WO | WO2012039787 A1 | 3/2012 |
| WO | WO2012039791 A1 | 3/2012 |
| WO | WO2012051570 A1 | 4/2012 |
| WO | WO2012142523 A3 | 10/2012 |
| WO | WO2013084165 A | 6/2013 |
| WO | WO2014033617 A1 | 3/2014 |
| WO | WO2014042433 A1 | 3/2014 |
| WO | WO2014078463 A2 | 5/2014 |
| WO | WO2014078778 A1 | 5/2014 |
| WO | WO2014116755 A1 | 7/2014 |
| WO | WO2014169280 A1 | 10/2014 |
| WO | 2015/069939 A1 | 5/2015 |
| WO | WO2016069825 A1 | 5/2016 |
| WO | WO2016069826 A1 | 5/2016 |
| WO | 2017/049060 A1 | 3/2017 |
| WO | WO2017184668 A1 | 10/2017 |

OTHER PUBLICATIONS

Cho, et al., Synthesis and antiviral activity of a series of 1'-substituted 4-aza-7,9-dideazaadenosine C-nucleosides, BioOrganic & Medicinal Chemistry Letters, Apr. 1, 2012, pp. 2705-2707, vol. 22, No. 8.
Kim, et al., Reversal of the Progression of Fatal Coronavirus Infection in Cats by a Broad-Spectrum Coronavirus Protease Inhibitor, PLOS Pathogens, Mar. 30, 2016, p. e1005531, vol. 12, No. 3.

(56) References Cited

OTHER PUBLICATIONS

Balzarini, et al., Inhibition of feline (FIPV) and human (SARS) coronavirus by semisynthetic derivatives of glycopeptide antibiotics, Antiviral Research, 2006, pp. 20-33, vol. 72, No. 1.
Burns, A glimmer of hope of fatal feline disease, JAVMA new, Dec. 15, 2017, pp. 1-5.
Murphy, et al., The nucleoside analog GS-441524 strongly inhibits feline infections peritonitis (FIP) virus in tissue culture and experimental cat infection studies, Veterinary Microbiology, ND, pp. 226-233, vol. 219.
Alessandrini, et al., Synthesis of Differently Protected 1-C-methyl-ribofuranoses Intermediates for the Preparation of Biologically Active 1'-C-methyl-ribonucleosides, Journal of Carbohydrate Chemistry, 2008, pp. 332-344, vol. 27, No. 5.
Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.
Arimilli, et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.
Asbun, et al., Synthesis of 5-substituted Pyrimidines. II, Journal of Organic Chemistry, 1968, pp. 140-142, vol. 31.
Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.
Bandini, et al., Indium tribromide: a highly effective catalyst for the addition of trimethylsilyl cyanide to α-hetero-substituted ketone, Tetrahedron Letters, 2001, pp. 3041-3043. vol. 42.
Barker, et al., 2,3,5-Tri-O-benzyl-D-ribosyl and -L-arabinosyl Bromides, Journal of Organic Chemistry, 1961, pp. 4605-4609, vol. 26, No. 11.
Barl, et al., The halogen/magnesium-exchange using iPrMgCl•LiCl and related exchange reagents, Heterocycles, Jan. 2014, pp. 827-844, vol. 88, No. 2.
Belokon, et al., Optimized catalysts for the asymmetric addition of trimethylsilyl cyanide to aldehydes and ketones, Tetrahedron, 2001, pp. 771-779, vol. 57.
Benksim, et al., A Novel Stereospecific Synthesis of Glycosyl Cyanides from 1,2-O-sulfinyl Derivatives, Organic Letters, 2004, pp. 3913-3915, vol. 6, No. 22.
Benzaria, et al., Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability, J. Med. Chem., 1996, pp. 4958-4965, vol. 39, No. 25.
Bio, et al., Practical Synthesis of a Potent Hepatitis C Virus RNA Replication Inhibitor, J. Org. Chem., 2004, pp. 6257-6266, vol. 69, No. 19.
Bobeck, et al., Advances in Nucleoside Monophosphate Prodrugs as Anti-HCV Agents, Antiviral Therapy, 2010, pp. 935-950, vol. 15.
Bojack, et al., Design and Synthesis of Inhibitors of Adenosine and AMP Deaminases, Organic Letters, 2001, pp. 839-842, vol. 3, No. 6.
Boyer, et al., Pathogenesis, diagnosis and management of hepatitis C, Journal of Hepatology, 2000, pp. 98-112, vol. 32.
Bozza, Zika Outbreak, Brazil 2015, ISARIC, 2015, 28 pages.
Brown, Progress towards improving antiviral therapy for hepatitis C virus polymerase inhibitors. Part O: Nucleoside analogues, 2009, pp. 709-725, vol. 18.
Bullard-Feibelman, et al., The FDA-approved drug Sofosbuvir inhibits Zika Virus infection, Antiviral Res., Jan. 1, 2018, pp. 134-140, vol. 137.
Butora, et al., Synthesis and HCV inhibitory properties of 9-deaza- and 7,9-dideaza-7-oxa-2'-C-methyladenosine, Bioorganic & Medicinal Chemistry, 2007, pp. 5219-5229, vol. 15, No. 15.

Cabirol, et al., Robust and Efficient, yet Uncatalyzed, Synthesis of Triarylsilyl-protected Cyanohydrins from Ketones, 2008, pp. 2446-2449, vol. 73.
Caira, Crystalline Polymorphism of Organic Compounds, Topics in Current Chemistry, 1998, pp. 163-208, vol. 198.
Calès, et al., Treatment of liver fibrosis: clinical aspects, Gastroentérologie Clinique et Biologique, 2009, pp. 958-966, vol. 33, No. 10-11.
Calisher, et al., Antigenic Relationships between Flaviviruses as Determined by Cross-neutralization Tests with Polyclonal Antisera, Journal of General Virology, 1989, pp. 37-43, vol. 70.
Camps, Studies on Structurally Simple -αβ-butenolides-II, Tetrahedron, 1982, pp. 2395-2402, vol. 38, No. 15.
Carroll, Robust Antiviral Efficacy upon Administration of a Nucleoside Analog to Hepatitis C Virus-Infected Chimpanzees, Antimicrobial Agents and Chemotherapy, 2009, pp. 926-934, vol. 53, No. 3.
Chapman, et al., RSV604, a Novel Inhibitor of Respiratory Syncytial Virus Replication, Antimicrobial Agents and Chemotherapy, 2007, pp. 3346-3353, vol. 51, No. 9.
Cho, et al., Discovery of the First C-Nucleoside HCV Polymerase Inhibitor (GS-6620) with Demonstrated Antiviral Response in HCV Infected Patients, J. Med. Chem., 2014, pp. 1812-1825, vol. 57, No. 5.
Cihlar, et al., Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131, Antimicrobial Agents and Chemotherapy, 2008, pp. 655-665, vol. 52, No. 2.
Clark, et al., Design, Synthesis, and Antiviral Activity of 2'-Deoxy-2'-fluoro-2'-C-methylcytidine, a Potent Inhibitor of Hepatitis C Virus Replication, Journal of Medicinal Chemistry, 2005, pp. 5504-5508, vol. 48, No. 17.
Colacino, et al., Synthesis and Biological Evaluation of Some 5-Nitro- and 5-Amino Derivatives of 2'-Deoxycytidine, 2',3'-Dideoxyuridine, and 2',3'-Dideoxycytidine, Nucleoside, Nucleotides & Nucleic Acids, 2003, pp. 2013-2026, vol. 22, No. 11.
Dai, et al., Synthesis of 2'-C-β-Fluoromethyluridine, Organic Letters, 2003, pp. 807-810, vol. 5, No. 6.
De Clercq, Antiviral Drugs: Current State of the Art, J. Clin. Virol., 2001, pp. 73-89, vol. 22, No. 1.
De Clercq, Molecular Targets for Antiviral Agents, The Journal of Pharmacology and Experimental Therapeutics, 2001, pp. 1-10, vol. 297, No. 1.
De Francesco, et al., Approaching a New Era for Hepatitis C Virus Therapy: Inhibitors of the NS3-4A Serine Protease and the NS5B RNA-Dependent RNA Polymerase, Antiviral Research, 2003, pp. 1-16, vol. 58, No. 1.
De Las Heras, Synthesis of Ribosyl and Arabinosyl Cyanides by Reaction of 1-O-Acyl Sugars with Trimethylsilyl Cyanide, Journal of the Chemical Society, Perkin Transactions 1, 1982, pp. 903-907.
De Lombaert, et al., N-Phosphonomethyl Dipeptides and Their Phosphonate Prodrugs, a New Generation of Neutral Endopeptidase (NEP, EC 3.4.24.11) Inhibitors, J. Med. Chem., 1994, pp. 498-511, vol. 37, No. 4.
Di Bisceglie, et al., The Unmet Challenges of Hepatitis C, Scientific American, Oct. 1999, pp. 80-85.
Dolzhenko, et al., Pyrazolo[1,5-a][1,3,5]Triazines(5-Aza-9-Deazapurines): Synthesis and Biological Activity, Heterocycles, 2008, pp. 1575-1622, vol. 75, No. 7.
Domingo, et al., The quasispecies (extremely heterogeneous) nature of viral RNA genome populations: biological relevance—a review, Gene, 1985, pp. 1-8, vol. 40.
Dondoni, et al., Thiazole-Based Synthesis of Formyl C-Glycosides, Journal of Organic Chemistry, 1994, pp. 6404-6414, vol. 59.
Dudfield, et al., Synthesis of C-ribosyl 1,2,4-triazolo[3,4f][1,2,4]triazines as Inhibitors of Adenosine and AMP Deaminasses, J. Chem. Soc., Perkin Trans. 1, 1999, pp. 2937-2942.
Dudfield, P. et al., Synthesis of C-ribosyl imidazo[2,1-f][1,2,4]triazines as inhibitors of adenosine and AMP deaminases, J. Chem. Soc, Perkin Trans I, 1999, pp. 2929-2936.
Dymock, et al., Novel approaches to the treatment of hepatitis C virus infection, Antiviral Chemistry & Chemotherapy, 2000, pp. 79-96, vol. 11, No. 2.

(56) References Cited

OTHER PUBLICATIONS

El Safadi, et al., 5-Modified-2'-dU and 2'-dC as Mutagenic Anti HIV-1 Proliferation Agents: Synthesis and Activity, Journal of Medicinal Chemistry, 2010, pp. 1534-1545, vol. 53, No. 4.
Farquhar, et al., Biologically Reversible Phosphate-Protective Groups, Journal of Pharmaceutical Sciences, 1983, pp. 324-325, vol. 72, No. 3.
Fukumoto, et al., Viral Dynamics of Hepatiis C Early After Orthotopic Liver Transplantation: Evidence for Rapid Turnover of Serum Virions, Hepatology, 1996, pp. 1351-1354, vol. 24.
Garcia, et al., Synthesis of (2,3,4,6-tetra-O-acetyl-alpha-D-glycopyranosyl)thiophene derivatives as new C-nucleoside analogues, J. Carbohydrate Chemistry, 2001, pp. 681-687, vol. 20, No. 7/8.
Gardelli, et al., Phosphoramidate Prodrugs of 2'-C-Methylcytidine for Therapy of Hepatitis C Virus Infection, Journal of Medicinal Chemistry, 2009, pp. 5394-5407, vol. 52, No. 17.
Gleeson, et al., Prediction of the Potency of Inhibitors of Adenosine Deaminase by QM/MM Calculations, Chem. Commun., 2003, pp. 2180-2181.
Gordon, et al., Control of Hepatitis C: A Medicinal Chemistry Perspective, J. Med. Chem., 2005, pp. 1-20, vol. 48, No. 1.
Greene, et al., Protective Groups in Organic Synthesis, 1991, pp. 118-142, John Wiley & Sons.
Gudmundsson, et al., Synthesis of imidazo[1,2-a]pyridine C-Nucleosides with an Unexpected Site of Ribosylation, Journal of Organic Chemistry, 1997, pp. 3453-3459, vol. 62.
Gudmundsson, et al., The Condensation of 2,6-dichloroimidazo[1,2-a]pyridine C-nucleoside with an Unexpected Site of Ribosylation, Tetrahedron Letters, 1996, pp. 2365-2368, vol. 7, No. 14.
Gunic, et al., Cyclic monophosphate prodrugs of base-modified 2'-C-methyl ribonucleosides as potent inhibitors of hepatitis C virus RNA replication, Bioorganic & Medicinal Chemistry Letters, 2007, pp. 2452-2455, vol. 17.
Hamann, et al., Synthesis and antiviral evaluation of 7,9-dideaza-8-thiapurine C-nucleoside derivatives, Collection Symposium Series, 2008, pp. 347-349, vol. 10.
Hamann, et al., Synthesis and antiviral evaluation of thieno[3,4-d]pyrimidine C-nucleoside analogues of 2',3'-dideoxy-and 2',3'-dideoxy-2',3'-didehydro-adenosine and -inosine, Bioorganic & Medicinal Chemistry, 2009, pp. 2321-2326, vol. 17.
Han, et al., Synthesis of 1-Chloroacetyl-1-dehydroxy-2,3,5-tri-O-benzoyl-β-D-ribofuranose. A Potentially Versatile Intermediate for the Synthesis of C-Nucleosides, Synthetic Communications, 1992, pp. 2815-2822, vol. 22, No. 19.
Haraguchi, K. et al., Stereoselective Synthesis of 1'-C-Branched Uracil Nucleosides From Uridine, Nucleosides & Nucleotides, 1995, pp. 417-420, vol. 14, No. 3-5.
Harki, et al., Synthesis and Antiviral Activity of 5-Substituted Cytidine Analogues: Identification of Potent Inhibitor of Viral RNA-Dependent RNA Polymerases, Journal of Medicinal Chemistry, 2006, pp. 6166-6169, vol. 49, No. 21.
Hayashi, et al., C-Nucleosides, A Synthesis of 2-Substituted 7-(b-D-Ribofuranosyl)-Pyrrolo[2,1-f]-1,2,4-Triazines. A New Type of "Purine Like" C-Nucleoside, Heterocycles, 1992, pp. 569-574, vol. 34, No. 3.
Hecker, et al., Liver Targeted Prodrugs of 2'-C-Methyladenosine for Therapy of Hepatitis C Virus Infection, J. Med. Chem., 2007, pp. 3891-3896, vol. 50, No. 16.
Hoffmann, et al., When, in the context of drug design, can a fluorine atom successfully substitute a hydroxyl group?, International Journal of Quantum Chemistry, 2002, pp. 419-427, vol. 89.
Itoh, et al., Divergent and Stereocontrolled Approach to the Synthesis of Uracil Nucleosides Branched at the Anomeric Position, J. Org. Chem., 1995, pp. 656-662, vol. 60.
Jasko, et al., 5'-Phosphonates of Ribonucleosides and 2'-Deoxyribonucleosides: Synthesis and Antiviral Activity, Nucleosides & Nucleotides, 1993, pp. 879-893, vol. 12, No. 8.

Kabat, et al., Nucleosides, CXLVIII, Synthesis of 6-(β-D-Ribofuranosyl)picolinamide: A Novel C-Nucleoside from D-Ribonolactone, Chemical & Pharmaceutical Bulletin, 1988, pp. 634-640, vol. 36, No. 2.
Khamnei, et al., Neighboring Group Catalysis in the Design of Nucleotide Prodrugs, J. Med. Chem., 1996, pp. 4109-4115, vol. 39, No. 20.
Klumpp, et al., The Novel Nucleoside Analog R1479 (4'-Azidocytidine) is a Potent Inhibitor of NS5B-dependent RNA Synthesis and Hepatitis C virus Replication in Cell Culture, Journal of Biological Chemistry, 2006, pp. 3793-3799, vol. 281, No. 7.
Knaggs, et al. A QSAR Study Investigating the Effect of L-Alanine Ester Variation on the Anti-HIV Activity of Some Phosphoramidate Derivatives of d4T, 2000, pp. 2075-2078.
Knutsen, et al., Synthesis of Imidazo-fused Bridgehead-nitrogen C—Nucleosides : Coupling-Elimination Reactions of 2,5-Anhydro-3,4,6-tri-O-benzoyl-D-allonic Acid, J. Chem. Soc. Perkin Trans I, 1985, pp. 621-630.
Knutsen, et al., Synthesis of Imidazo-fused Bridgehead-nitrogen C—Nucleosides via Dehydrative Coupling Reactions of 2,5-Anhydro-3,4,6-tri-O-benzoyl-D-allonic Acid, J. Chem. Soc. Perkin Trans I, 1984, pp. 229-238.
Kobe, et al., Use of Distance Geometry Approach for the In Vitro Antiviral Activity Evaluation of N-bridgehead C-nucleosides, European J. Med. Chem., 1992, pp. 259-266, vol. 27, No. 3.
Lefebvre, et al., Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate, Journal of Medicinal Chemistry, 1995, pp. 3941-3950, vol. 38, No. 20.
Lefebvre, et al., Synthesis, Decomposition Pathways and 'In Vitro' Evaluation of Bioreversible Phosphotriesters of Azt, Nucleosides, Nucleotides & Nucleic Acids, 1995, pp. 763-766, vol. 14, No. 3-5.
Lindell, et al., Synthesis and Biochemical Testing of 3-(Carboxyphenylethyl)imidazo[2,1-f][1,2,4]triazines as Inhibitors of AMP Deaminase, ACS Medicinal Chemistry Letters, 2010, pp. 286-289, vol. 1, No. 6.
Lovelette, 1,2,4-Triazines. Synthesis of selected members of the s-triazolo[3,4-f][1,2,4]triazine and tetrazolo[1,5-f][1,2,4]triazine ring systems, Journal of Heterocyclic Chemistry, 1979, pp. 555-560, vol. 16.
Lu, Chengping, Veterinary Microbiology 5th edition, Jan. 31, 2013, p. 431, China Agriculure Press (No English Translation available).
Martell, et al., Hepatitis C Virus (HCV) Circulates as a Population of Different but Closely Related Genomes: Quasispecies Nature of HCV Genome Distribution, Journal of Virology, 1992, pp. 3225-3229, vol. 6695.
Mason, et al., Polyadenylation-dependent screening assay for respiratory syncytial virus RNA transcriptase activity and identification of an inhibitor, Nucleic Acids Research, 2004, pp. 4758-4767, vol. 32, No. 16.
Matulic-Adamic, et al., Synthesis of 3-(β-D-Ribofuranosyl)-2-Fluoropyridine and 3-(β-D-Ribofuranosyl)-Pyridin-2-one, Tetrahedron Letters, 1997, pp. 203-206, vol. 38, No. 2.
Matulic-Adamic, et al., Synthesis of 5-(β-D-Ribofuranosyl)-Pyridin-2-one: a 'Deletion-Modified' Analogue of Uridine, Tetrahedron Letters, 1997, pp. 1669-1672, vol. 38, No. 10.
McGuigan, et al. Application of Phosphoramidate ProTide Technology Significantly Improves Antiviral Potency of Carbocyclic Adenosine Derivatives, 2006, pp. 7215-7226.
McGuigan, et al., Intracellular Delivery of Bioactive AZT Nucleotides by Aryl Phosphate Derivatives of AZT, J. Med. Chem., 1993, pp. 1048-1052, vol. 36, No. 8.
Meppen, et al., Cyclic phosphoramidates as prodrugs of 2'-C-methylcytidine, European Journal of Medicinal Chemistry, 2009, pp. 3765-3770, vol. 49, No. 9.
Meppen, et al., Medi-404—A Prodrug Approach for the Treatment of HCV Infection, Abstracts of papers, 236th ACS National Meeting, Philadelphia, PA, United States, Aug. 17-21, 2008.
Metobo, et al., Practical synthesis of 1'-substituted Tubercidin C-nucleoside analogs, Tetrahedron Letters, Feb. 2012, pp. 484-486, vol. 53, No. 5.

(56) References Cited

OTHER PUBLICATIONS

Migliaccio, et al., Characterization of Resistance to Non-obligate Chain-terminating Ribonucleoside Analogs That Inhibit Hepatitis C Virus Replication in vitro, The Journal of Biological Chemistry, 2003, pp. 49164-49170, vol. 278, No. 49.
Mitchell, et al., Bioreversible Protection for the Phospho Group: Bioactivation of the Di(4-acyloxybenzyl) and Mono(4-acyloxybenzyl) Phosphoesters of Methylphosphonate and Phosphonoacetate, J. Chem. Soc., Perkin Trans. 1, 1992, pp. 2345-2353.
Mitchell, et al., Synthesis of C-Nucleoside Isosteres of 9-(2-Hydroxyethoxymethyl)guanine (Acyclovir), J. Het. Chem., 1984, pp. 697-699, vol. 21, No. 3.
Moennig, et al., The Pestiviruses, Advances in Virus Research, 1992, pp. 53-98, vol. 41.
Moradpour, et al., Replication of hepatitis C virus, Nature Reviews Microbiology, 2007, pp. 453-463, vol. 5, No. 6.
Moscow, et al., Reduced Folate Carrier Gene (RFC1) Expression and Anti-Folate Resistance in Transfected and Non-Selected Cell Lines, International Journal of Cancer, 1997, pp. 184-190, vol. 72.
Murakami, et al., Mechanism of Activation of Beta-D-2'-Fluoro-2'-C-Methylcytidine and Inhibition of Hepatitis C Virus NS5B RNA Polymerase, Antimicrob Agents Chemother., Feb. 2007, pp. 503-509, vol. 51, No. 2.
Neumann, et al., Hepatitis C Viral Dynamics in Vivo and the Antiviral Efficacy of Interferon-α Therapy, Science, 1998, pp. 103-107, vol. 282.
Nishimura, et al., Synthesis of pyrrolo[2,1-f][1,2,4]triazine C-nucleosides. Isosteres of sangivamycin, tubercidin, and toyocamycin, Carbohydrate Research, 2001, pp. 77-82, vol. 331.
Ogura, et al., Reaction of Ethynyl Compounds with Lactones, Journal of Organic Chemistry, 1972, pp. 72-75, vol. 37, No. 1.
Otter, B. et al., Conformational Properties of Purine-Like C-Nucleosides, Nucleosides & Nucleotides, 1996, pp. 793-807, vol. 15, No. 1-3.
Pankiewicz, et al., C-Nucleoside Analogues of Nicotinamide Mononucleotide (NMN), Nucleosides and Nucleotides, 1988, pp. 589-593, vol. 7, No. 5&6.
Pankiewicz, et al., Efficient Synthesis of 5-(β-D-Ribofuranosyl)nicotinamide and its α-Isomer, Journal of Organic Chemistry, 1988, pp. 3473-3479, vol. 53.
Patil, et al., C-Glycosylation of Substituted Heterocycles under Friedel-Crafts Conditions (II): Robosylation of Multi-Functionalized Thiophenes and Furans for the Synthesis of Purine-Like C-Nucleosides, Nucleosides & Nucleotides, 1990, pp. 937-956, vol. 9, No. 7.
Patil, et al., Synthesis of Pyrrolo[2,1-f][1,2,4]triazine Congeners of Nucleic Acid Purines via the N-Amination of 2-Substituted Pyrroles, J. Het. Chem., 1994, pp. 781-786, vol. 31.
Patil, et al., Synthesis of some new thieno[3,4-d]pyrimidines and their C-nucleosides, Journal of Heterocyclic Chemistry, 1993, pp. 509-515, vol. 30, No. 2.
Patil, S. et al., 4-Aza-7,9-Dideazaadenosine, a New Cytotoxic Synthetic C-Nucleoside Analogue of Adenosine, Tetrahedron Letters, 1994, pp. 5339-5342, vol. 35, No. 30.
Perrone, et al., Application of the Phosphoramidate ProTide Approach to 4'Azidouridine Confers Sub-micromolar Potency versus Hepatitis C Virus on an Inactive Nucleoside, Journal of Medicinal Chemistry, 2007, pp. 1840-1849, vol. 50, No. 8.
Piccirilli, et al., A Direct Route to 3-(D-Ribofuranosyl)pyridine Nucleosides, Helvetica Chimica Acta, 1991, pp. 397-406, vol. 74.
Pierra, et al., Synthesis and Pharmacokinetics of Valopicitabine (NM283), and Efficient Prodrug of the Potent Anti-HCV Agent 2'-C-Methylcytidine, Journal of Medicinal Chemistry, 2006, pp. 6614-6620, vol. 49, No. 22.
Poduch, et al., Design of Inhibitors of Orotidine Monophosphate Decarboxylase Using Bioisosteric Replacement and Determination of Inhibition Kinetics, Journal of Medicinal Chemistry, 2006, pp. 4937-4945, vol. 49, No. 16.
Porter, et al., Zika virus, drug discovery, and student projects, ScienceBlogs, Mar. 9, 2016, 7 pages.
Puech, et al., Intracellular Delivery of Nucleoside Monophosphates through a Reductase-mediated Activation Process, Antiviral Research, 1993, pp. 155-174, vol. 22, No. 4.
Ramasamy, et al., Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor, J. Med. Chem., 1986, pp. 2231-2235, vol. 29, No. 11.
Rao, et al., C-Glycosylation of Substituted Heterocycles under Friedel-Crafts Conditions (I): A Two-Step Synthesis of the Thieno[3,4-d]Pyrimidine C-Nucleoside Analog of Inosine, Tetrahedron Letters, 1988, pp. 3537-3540, vol. 29, No. 29.
Reddy, et al., Stereoselective Synthesis of Nucleoside Monophosphate HepDirectTM Prodrugs, Tet. Lett., 2005, pp. 4321-4324, vol. 46.
Sacramento, et al., The clinically approved antiviral drug Sofosbuvir inhibits Zika Virus replication, Nature, Jan. 18, 2017.
Schul, et al., A Dengue Fever Viremia Model in Mice Shows Reduction in Viral Replication and Suppression of the Inflammatory Response after Treatment with Antiviral Drugs, Journal of Infectious Diseases, 2007, pp. 665-674, vol. 195.
Schultz, Prodrugs of Biologically Active Phosphate Esters, Bioorganic & Medicinal Chemistry, 2003, pp. 885-898, vol. 11.
Scott, et al., Interferon-a-2b Plus Ribavirin: A Review of its Use in the Management of Chronic Hepatitis C, Drugs, 2002, pp. 507-556, vol. 62, No. 3.
Shekunov, et al., Crystallization processes in pharmaceutical technology and drug delivery design, Journal of Crystal Growth, 2000, pp. 122-136, vol. 211.
Siegel, Discovery and Synthesis of a Phosphoramidate Prodrug of a Pyrrolo[2,1-f][triazin-4-amino] Adenine C-Nucleoside(GS-5734) for the Treatment of Ebola and Emerging Viruses, J. Med. Chem., Jan. 26, 2017, 51 pages.
Silverman et al., The Organic Chemistry of Drug Design and Drug Action, 1992, pp. 19-23.
Silverman, The Organic Chemistry of Drug Design and Drug Action, 2nd Ed., 2004, pp. 29-34.
Srivastav, et al., Antiviral Activity of Various 1-(2'-Deoxy-β-D-lyxofuranosyl), 1-(2'-Fluoro-β-D-xylofuranosyl), 1-(3'- Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication, Journal of Medicinal Chemistry, 2010, pp. 7156-7166, vol. 53, No. 19.
Tapia, et al., Combination of a Mutagenic Agent with a Reverse Transcriptase Inhibitor Results n Systematic Inhibition of HIV-1 Infection, Virology, 2005, pp. 1-8, vol. 338.
Uchiyama, et al., O-selective Phosphorylation of Nucleosides without N-protection, J. Org. Chem., Jan. 1, 1993, vol. 58, No. 2.
Vaghefi, et al., Synthesis and Antiviral Activity of Certain Nucleoside 5'-Phosphonoformate Derivatives, Journal of Medicinal Chemistry, 1986, pp. 1389-1393, vol. 29, No. 8.
Venkatachalam, et al. Effect of change in nucleoside structure on the activation and antiviral activity of phosphoramidate derivatives, 2005, pp. 5408-5423.
Warren, et al., Therapeutic efficacy of the small molecules GS-5734 against EBOLA virus in rhesus monkeys, Nature, Mar. 17, 2016, 19 pages.
Wu, et al., Synthetic Methodologies for C-Nucleosides, Synthesis, 2004, pp. 1533-1553, vol. 10.
Yamanaka, et al., Metabolic Studies on BMS-200475, a New Antiviral Compound Active against Hepatitis B Virus, Antimicrobial Agents and Chemotherapy, 1999, p. 190, vol. 43, No. 1.
Yoshimura, et al., Synthesis and Biological Evaluation of 1'-C-Cyano-Pyrimidine Nucleosides, Nucleosides & Nucleotides, 1996, pp. 305-324, vol. 15, No. 1-3.
Zhang, et al., A Practical Synthesis of (2R)-3,5-di-O-benzoyl-2-fluoro-2-C-methyl-D-ribono-y-lactone, Tetrahedron: Asymmetry, 2009, pp. 305-312, vol. 20.

\* cited by examiner

METHODS OF TREATING FELINE CORONAVIRUS INFECTIONS

CROSS-REFERENCES TO RELATED APPLICATIONS

This application claims priority to U.S. Provisional Application No. 62/470,944, filed Mar. 14, 2017, which is incorporated in its entirety herein for all purposes.

FIELD

The invention relates generally to methods and compounds for treating feline Coronavirus infections, particularly methods for treating feline infectious peritonitis virus (FIPV).

BACKGROUND

Feline coronavirus (FCoV) belongs to the Coronaviridae family, a group of enveloped, positive stranded RNA viruses, commonly found in cats. In nature, FCoVexists as two distinct biotypes: feline enteric coronavirus (FECV) and feline infectious peritoneal virus (FIPV), a mutated form of FECV.

FECV infection is widespread in cats, with an estimated 40-80% of cats shedding the virus worldwide. FECV chronically infects the gastrointestinal epithelial cells in cats and is typically transmitted through the fecal-oral route. FECV infection in cats is largely asymptomatic, with some cats experiencing diarrhea, vomiting, loss of appetite, and fever.

The FIPV biotype arises following a single nucleotide polymorphism or deletion that inactivates the viral 3c protease gene in FECV, although mutations within the viral spike protein has also been implicated. Inactivation of the 3c protease alters cell tropism enables the virus to replicate within macrophages, facilitating systemic dissemination of FIPV and the onset of feline infectious peritonitis (FIP).

FIP is a progressive, immune related disease in cats. FIP disease can take the form of "wet" or "dry" FIP. Wet FIP is associated with an inflammation of the visceral serosa and omentum resulting in the exudation of fluids into the abdomen and/or chest cavities. Dry FIP is characterized by granulomatous involvement of paracnchymatous organs such as the liver, central nervous system or eyes. The development of either the wet or dry form of FIP is invariably fatal.

FIP is a major problem in environments with large cat densities such as, multi-cat households, catteries, shelters, and cat rescue facilities. The disease is most prevalent in younger cats (<3 years old), and particularly kittens, due to the higher levels of replicating FECV, which increases the likelihood of mutation to the FIPV biotype, as well as reduced resistance to viruses harboring those mutations. FIP is a leading cause of death in cats under 2 years of age and is estimated to kill between 0.3 and 1% of cats worldwide.

Currently, there are no approved vaccines or effective antiviral therapies for the treatment of FIP. Therefore there is a significant need for the development of compounds to treat FIP in cats. Without being bound, it is hypothesized that treating FCoV or FIPV would prevent or treat FIP.

BRIEF SUMMARY OF THE INVENTION

In some embodiments, the present invention provides a method of treating a feline Coronavirus infection comprising administering a therapeutically effective amount of a compound:

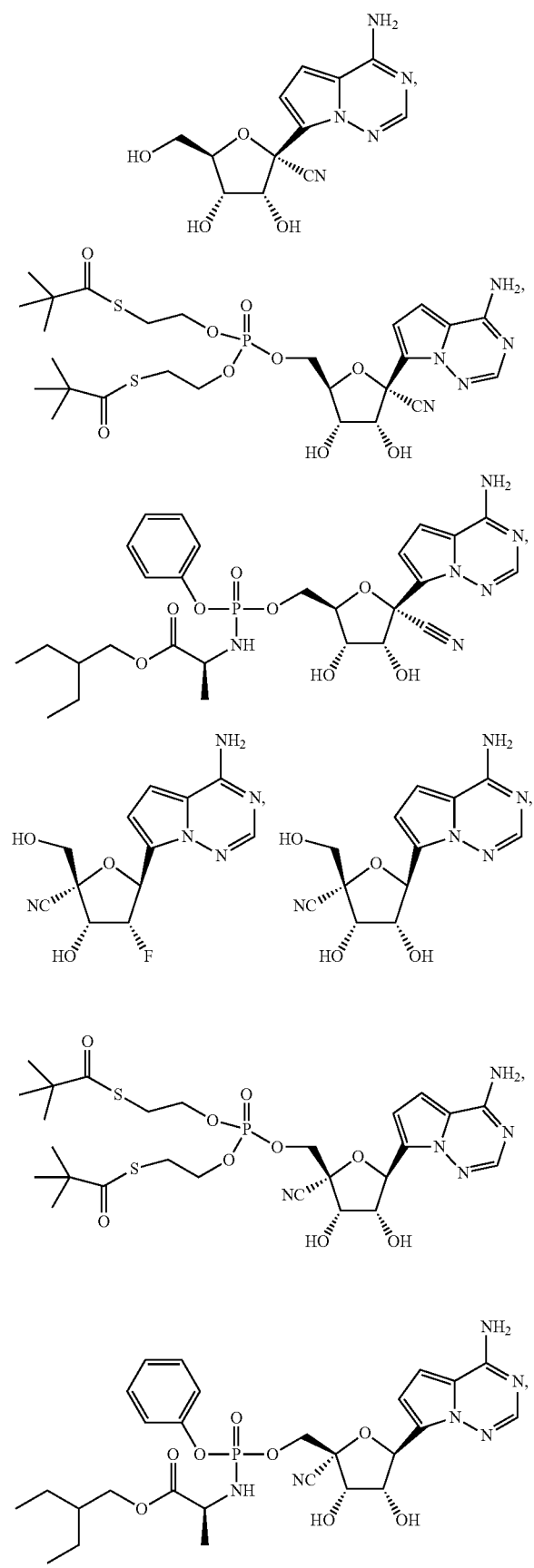

-continued

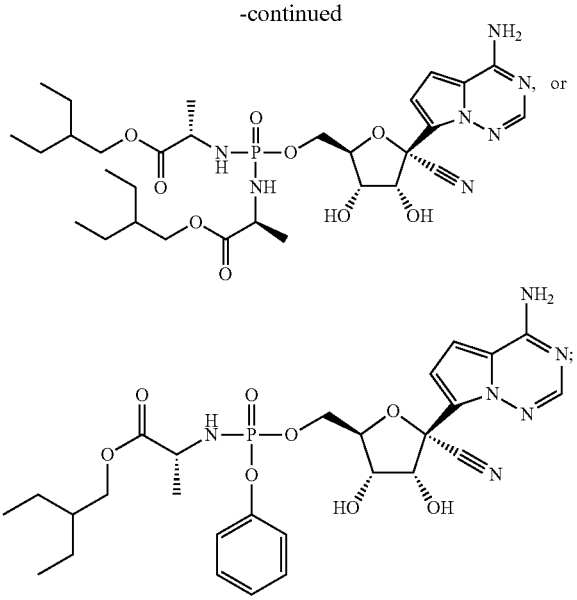

or a pharmaceutically acceptable salt thereof.

Provided is a method of treating a feline Coronavirus infection comprising administering a therapeutically effective amount of

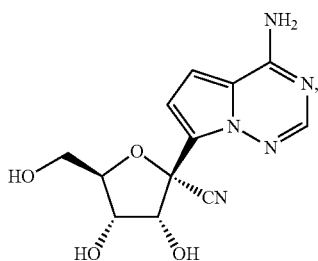 [SMILES: N#C[C@@]1(c2ccc3c(N)ncnn23)O[C@H](CO)[C@@H](O)[C@H]1O]

or a pharmaceutically acceptable salt thereof.

DETAILED DESCRIPTION OF THE INVENTION

I. Definitions

Figure 1:
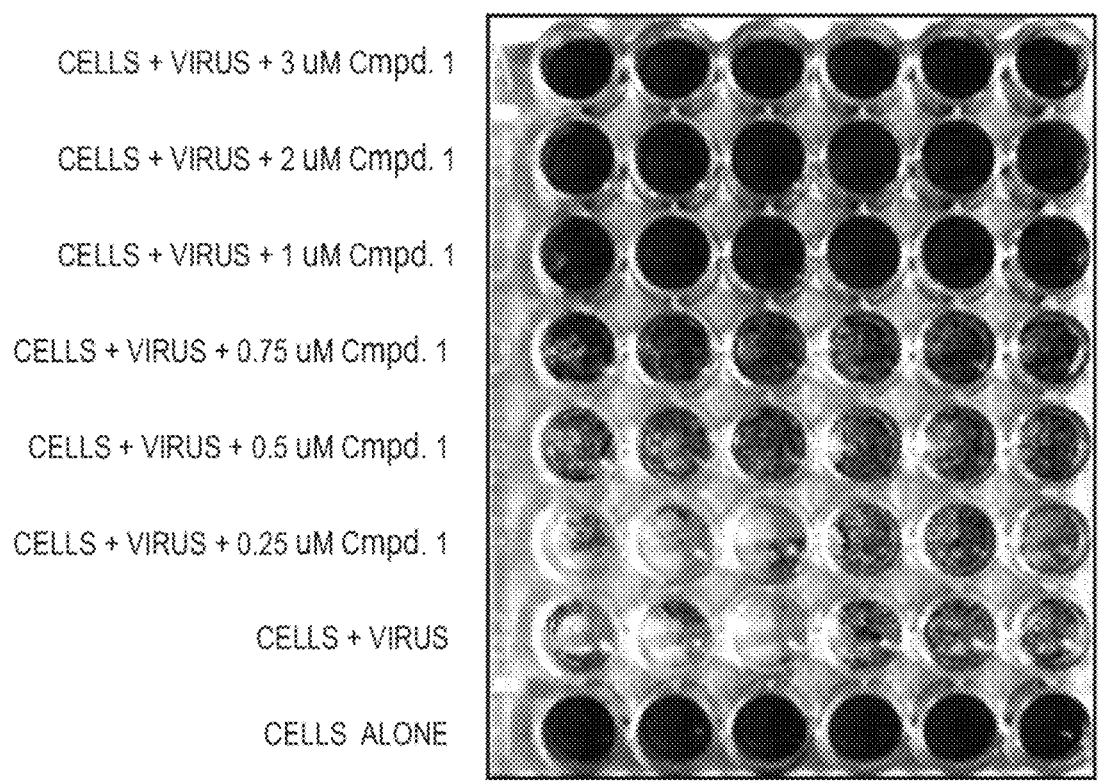
FIG. 1 shows inhibition of feline coronavirus in CRFK cells with Compound 1, with nearly 100% inhibition at 3, 2 and 1 μM; an EC50 of 0.75 μM.
Figure 2:
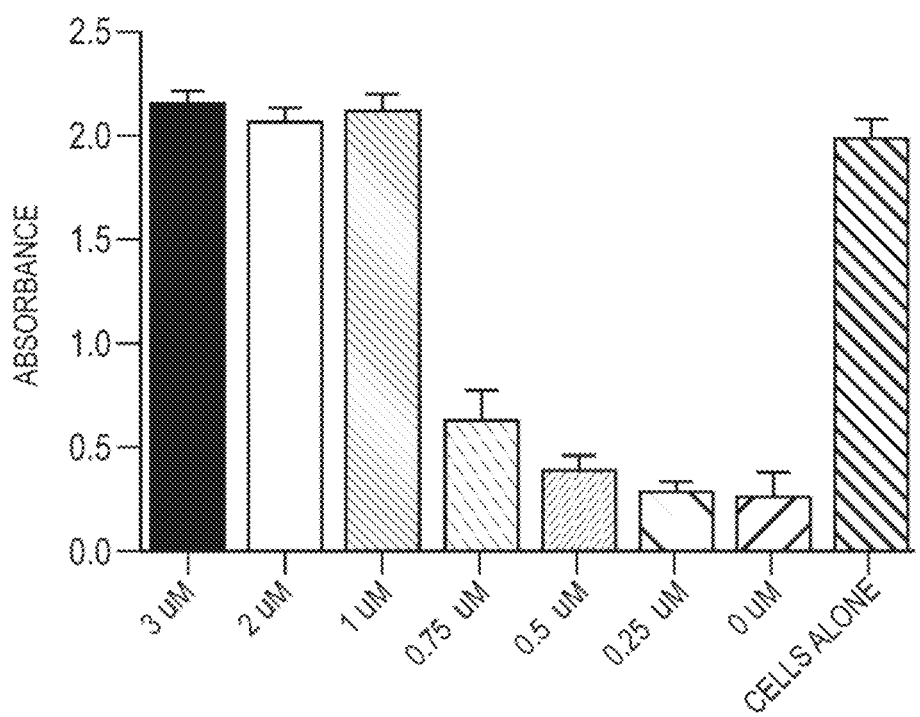
FIG. 2 shows the antiviral activity of Compound 1 against FIPV in CRFK cells.
Figure 3:
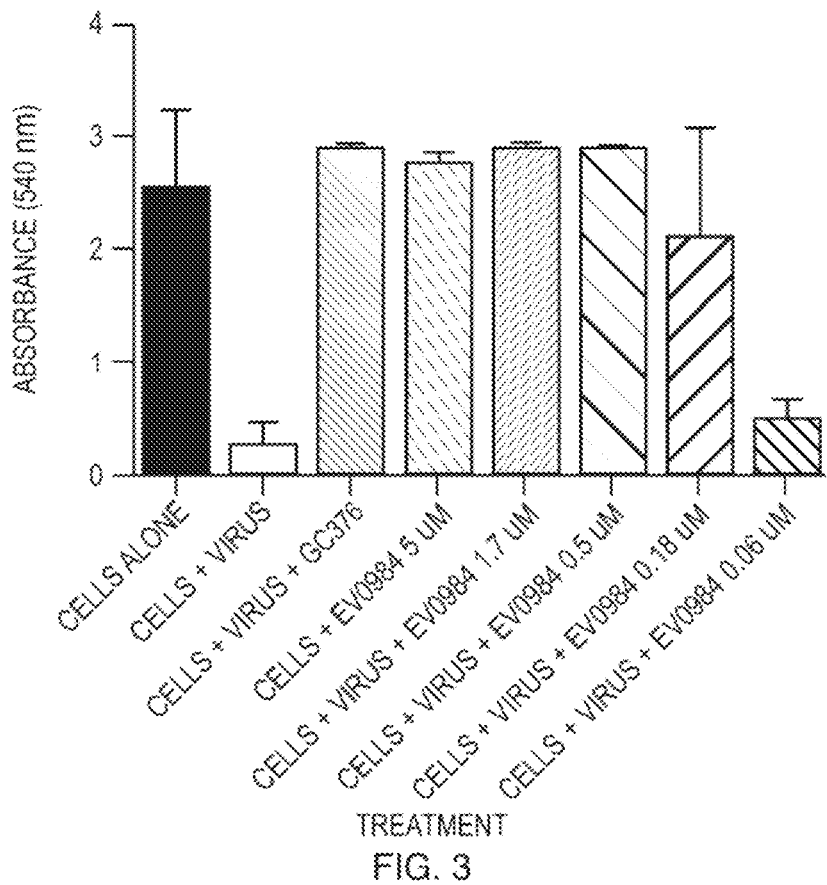
FIG. 3 shows the antiviral activity of Compound 1 against FIPV in CRFK cells.
Figure 4:
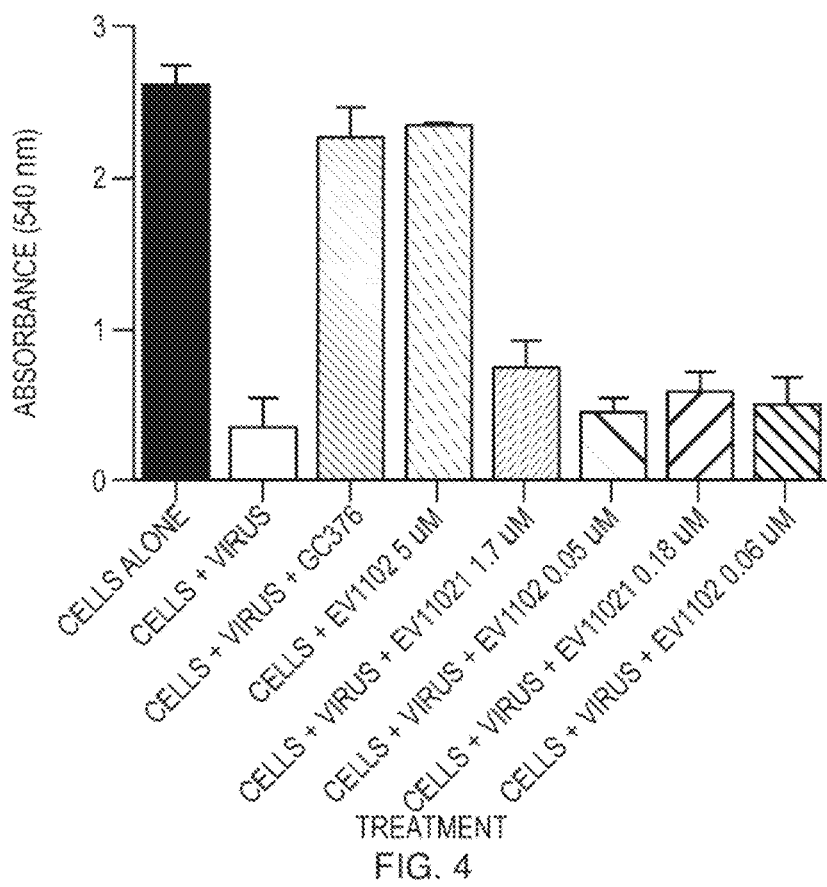
FIG. 4 shows the antiviral activity of Compound 2 against FIPV in CRFK cells.
Figure 5:
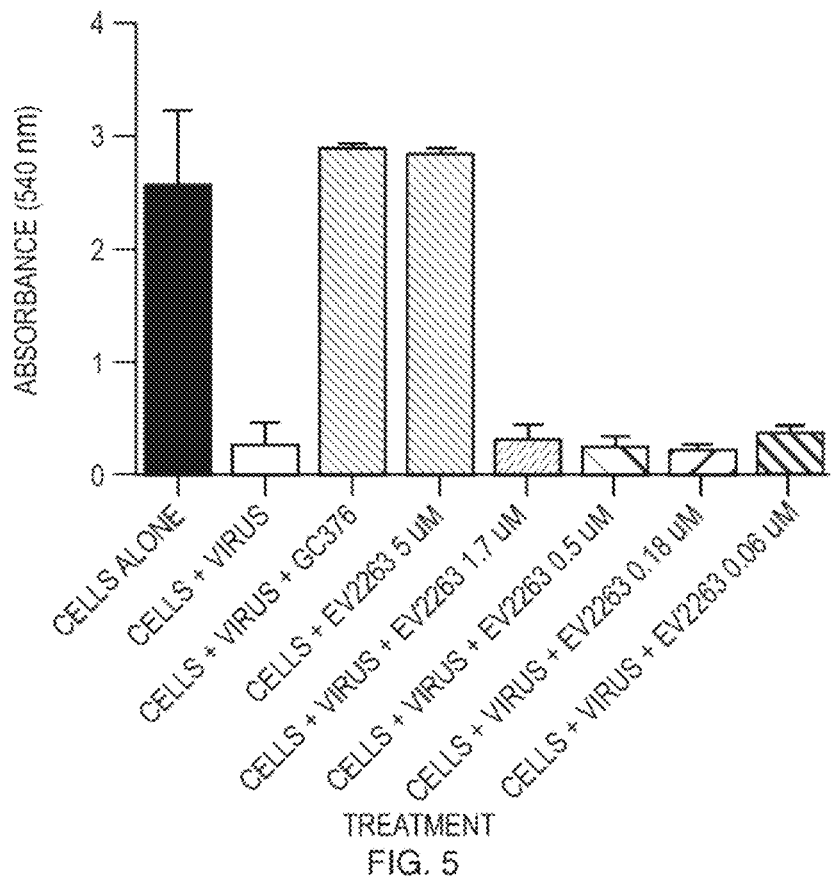
FIG. 5 shows the antiviral activity of Compound 9 against FIPV in CRFK cells.
Figure 6:
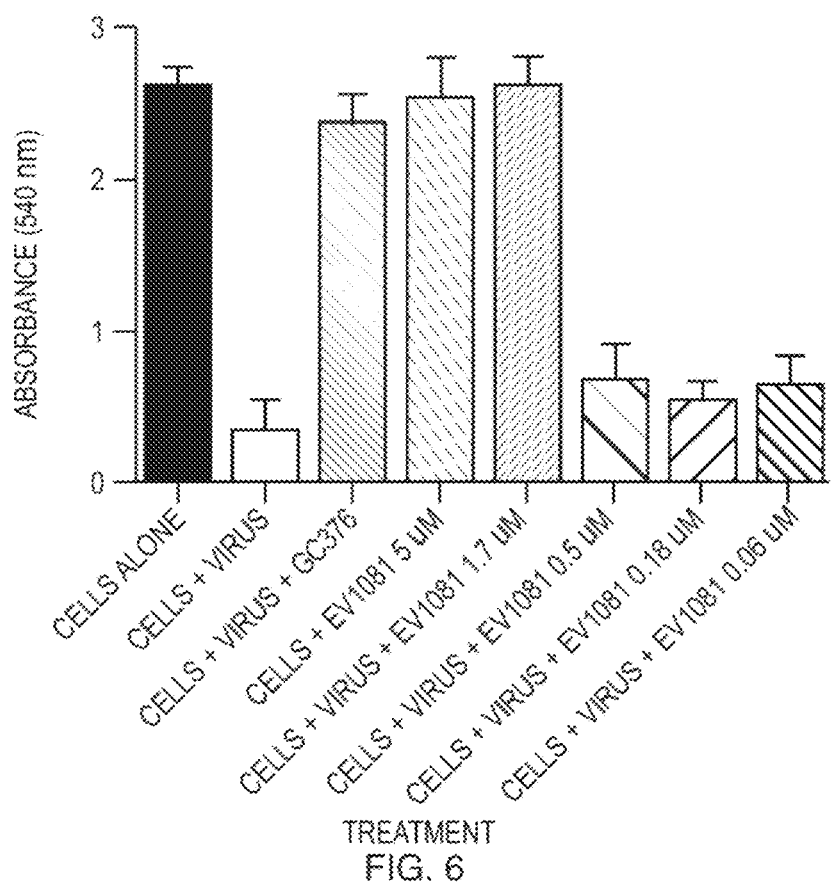
FIG. 6 shows the antiviral activity of Compound 3 against FIPV in CRFK cells.
Figure 7:
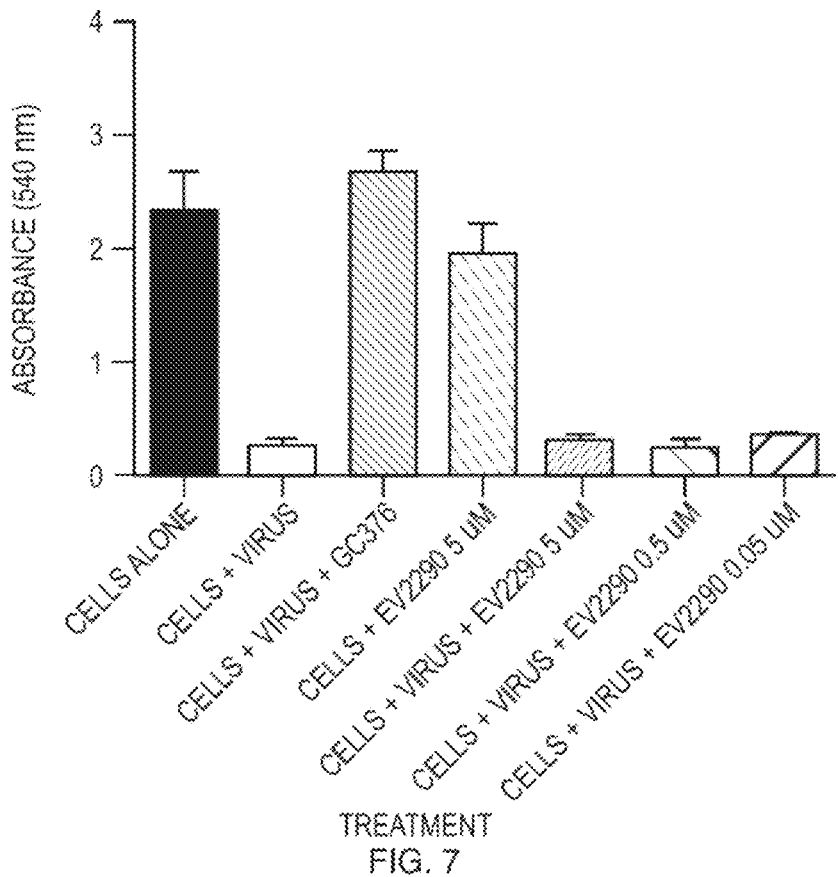
FIG. 7 shows the antiviral activity of Compound 6 against FIPV in CRFK cells.
Figure 8:
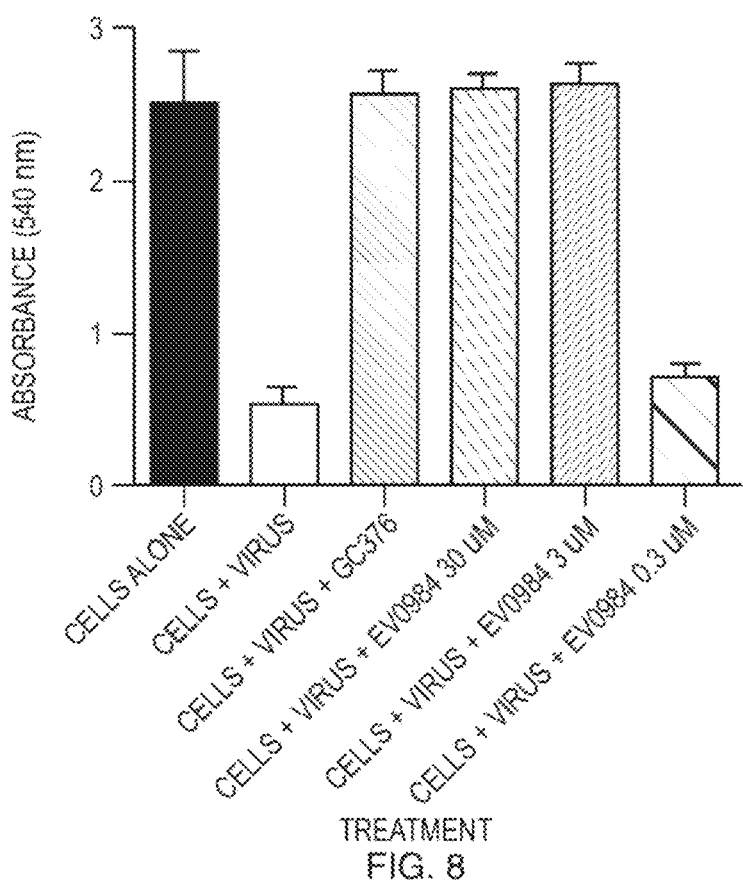
FIG. 8 shows the antiviral activity of Compound 1 against FIPV in CRFK cells.
Figure 9:
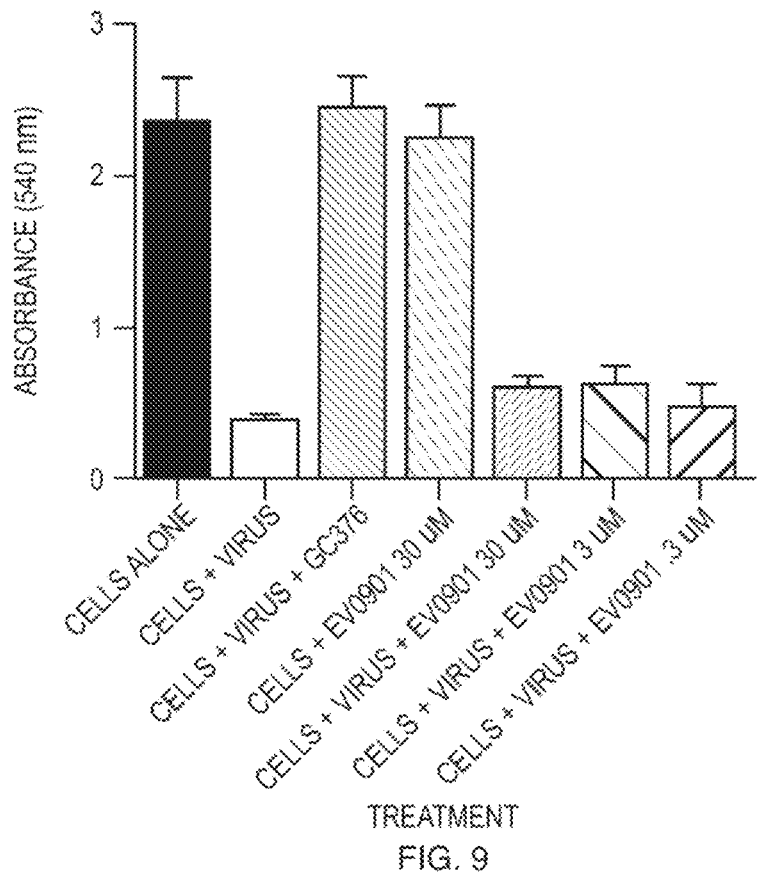
FIG. 9 shows the antiviral activity of Compound 4 against FIPV in CRFK cells.
Figure 10:
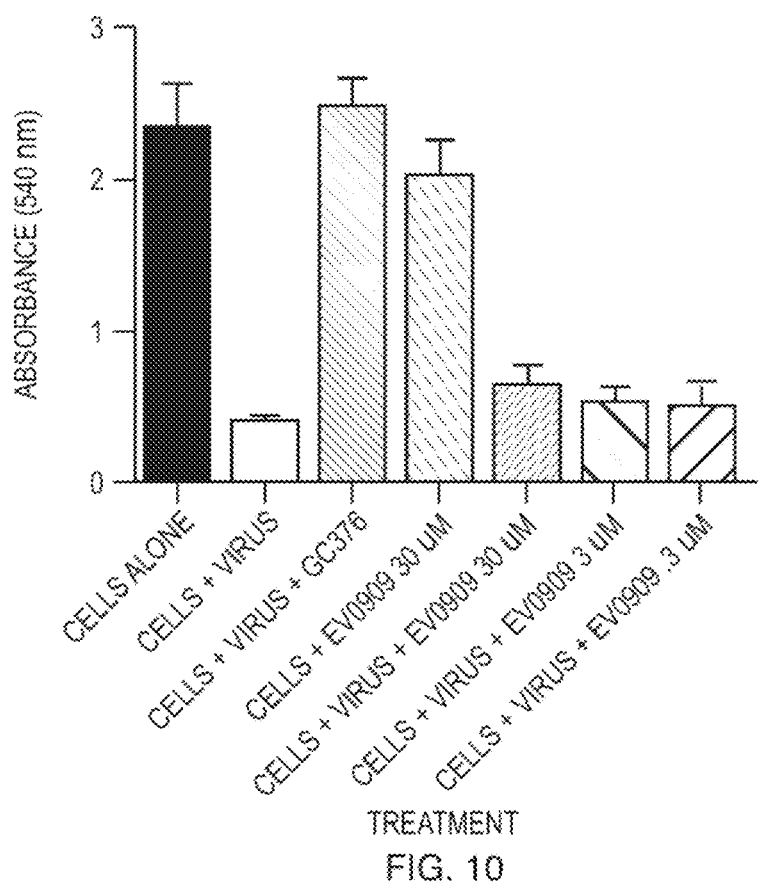
FIG. 10 shows the antiviral activity of Compound 5 against FIPV in CRFK cells.
Figure 11:
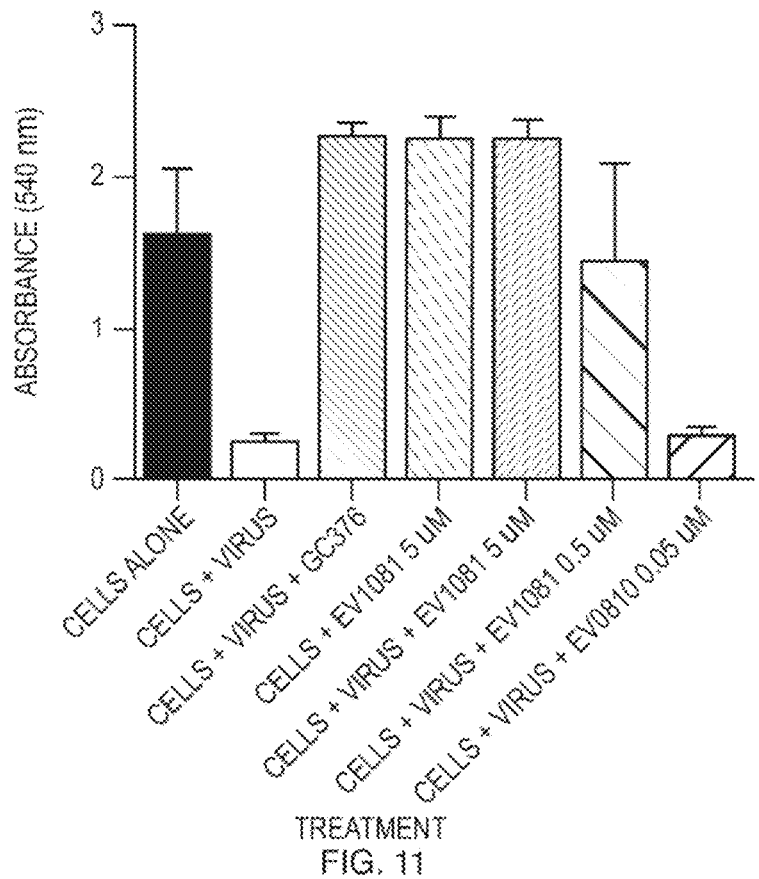
FIG. 11 shows the antiviral activity of Compound 3 against FIPV in CRFK cells.
Figure 12:
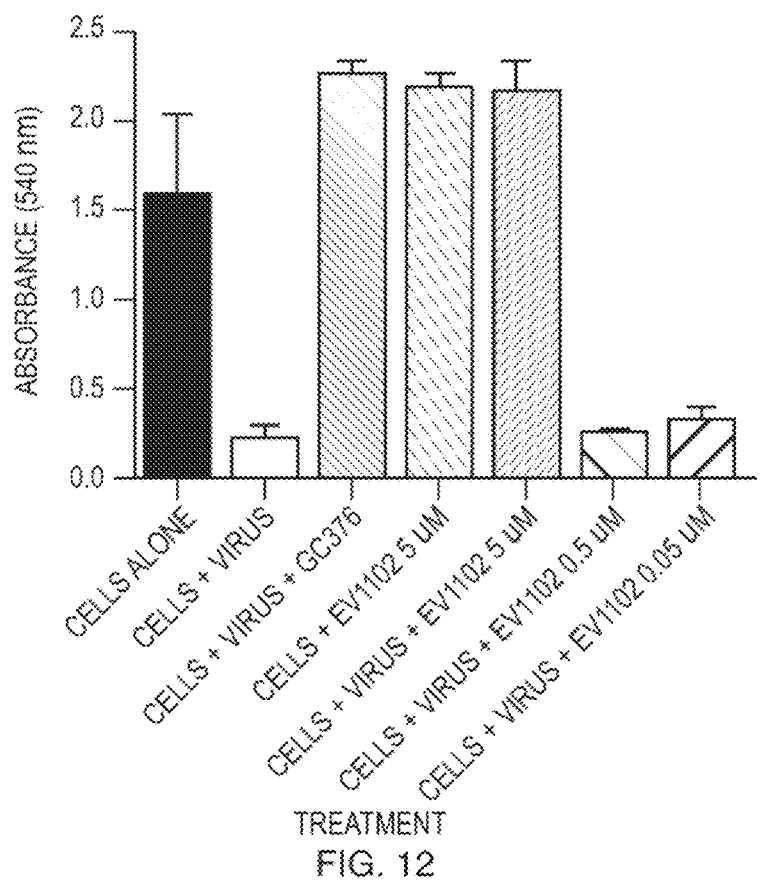
FIG. 12 shows the antiviral activity of Compound 2 against FIPV in CRFK cells.
Figure 13:
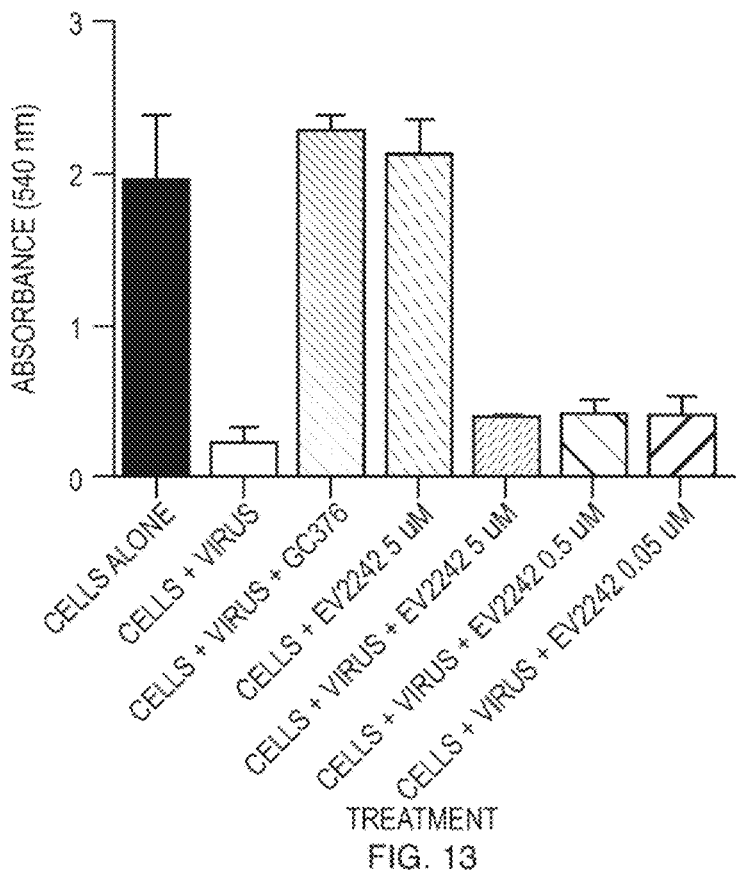
FIG. 13 shows the antiviral activity of Compound 7 against FIPV in CRFK cells.
Figure 14:
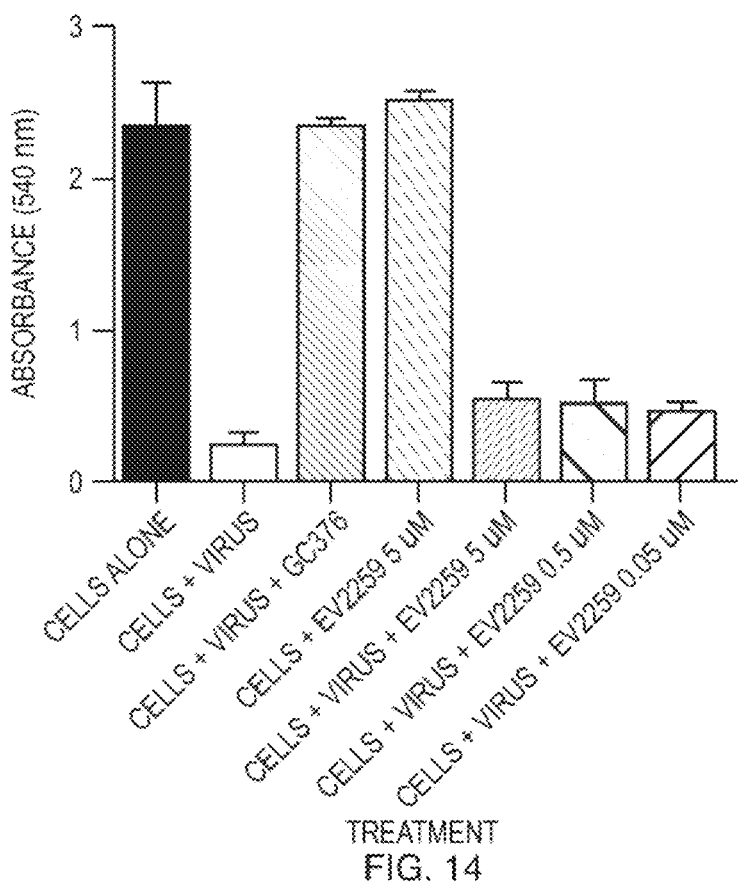
FIG. 14 shows the antiviral activity of Compound 8 against FIPV in CRFK cells.
Figure 15:
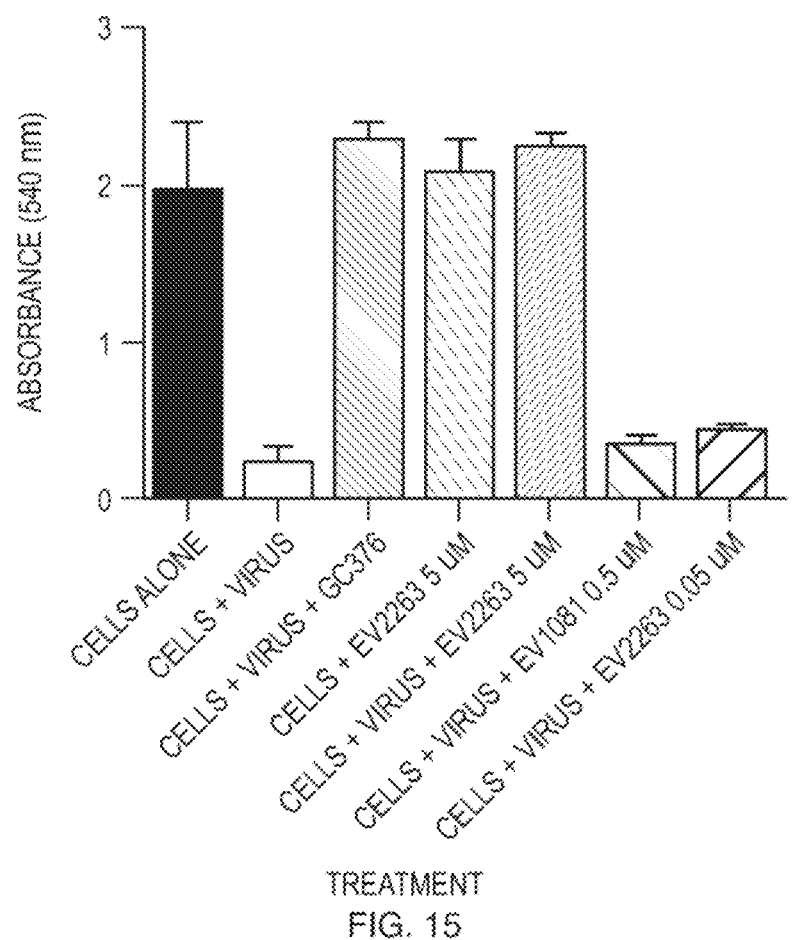
FIG. 15 shows the antiviral activity of Compound 9 against FIPV in CRFK cells.

Unless stated otherwise, the following terms and phrases as used herein are intended to have the following meanings:

The term "treating" or "treatment", as used herein, unless otherwise indicated, means reversing, alleviating, inhibiting the progress of, or preventing the disorder or condition to which such term applies, or one or more symptoms of such disorder or condition.

The term "therapeutically effective amount", as used herein, is the amount of Compound 1, or a pharmaceutically acceptable salt thereof, present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the specific activity of the composition, the delivery device employed, the physical characteristics of the composition, its intended use, as well as animal considerations such as severity of the disease state, veterianian cooperation, etc., and can readily be determined by one skilled in the art based upon the information provided herein.

Reference to Compound 1, or Compounds 2 to 9, described herein may also includes a reference to a pharmaceutically acceptable salt thereof. Examples of pharmaceutically acceptable salts include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Pharmaceutically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalene-disulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Pharmaceutically acceptable salts of a compound of a hydroxy group include the anion of said compound in combination with a suitable cation such as $Na^+$ and $NR_4^+$.

Compound 1, and Compounds 2 to 9, or a pharmaceutically acceptable salt thereof, may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of Compound 1 or pharmaceutically acceptable salts thereof.

Compound 1, and Compounds 2 to 9, and pharmaceutically acceptable salts thereof may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. In some embodiments, the invention comprises all amorphous forms of Compound 1 or pharmaceutically acceptable salts thereof.

In some embodiments, Compound 1, and Compounds 2 to 9, or a pharmaceutically acceptable salt thereof, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatmentarean.

The disclosure also includes Compound 1, and Compounds 2 to 9, in which from 1 to n hydrogens attached to a carbon atom is/are replaced by deuterium, in which n is the number of hydrogens in the molecule. Such compounds exhibit increased resistance to metabolism and are thus useful for increasing the half-life of Compound 1 when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

II. Treating Feline Coronavirus

Reference will now be made in detail to certain embodiments, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

A. Compounds

Compounds useful in the methods of the present include the following:

| COMPOUND NO. | STRUCTURE | NAME |
|---|---|---|
| 1 (EV9084) | 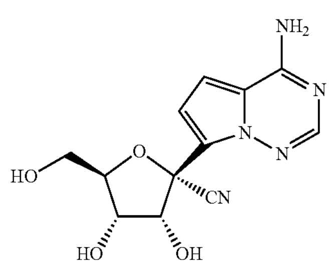 [SMILES: N#C[C@@]1(c2ccc3c(N)ncnn23)O[C@H](CO)[C@@H](O)[C@H]1O] | (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile |

| COMPOUND NO. | STRUCTURE | NAME |
|---|---|---|
| 2 (EV1102) | 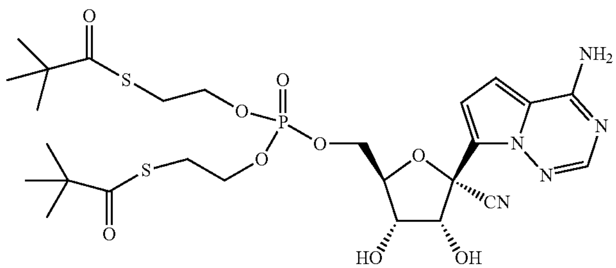 [SMILES: CC(C)(C)C(=O)SCCOP(=O)(OCCSC(=O)C(C)(C)C)OC[C@H]1O[C@@](C#N)(c2ccc3c(N)ncnn23)[C@H](O)[C@@H]1O] | ((((2R,3S,4R,5R)-5-(4-aminopyrrolo[2,1-f][1,2,4]triazin-7-yl)-5-cyano-3,4-dihydroxytetrahydrofuran-2-yl)methoxy) (S,S'-(((hydroxyphosphoryl)bis(oxy))bis(ethane-2,1-diyl))bis(2,2-dimethylpropanethioate)) |
| 3 (EV1081) | 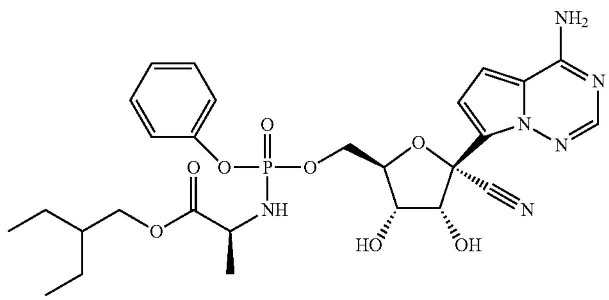 [SMILES: CCC(CC)COC(=O)[C@H](C)NP(=O)(OC[C@H]1O[C@@](C#N)(c2ccc3c(N)ncnn23)[C@H](O)[C@@H]1O)Oc1ccccc1] | 2-ethylbutyl ((((2r,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate |
| 4 (EV0901) | 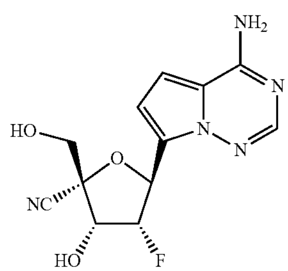 [SMILES: N#C[C@]1(CO)O[C@@H](c2ccc3c(N)ncnn23)[C@H](F)[C@@H]1O] | (2R,3R,4R,5S)-5-(4-aminopyrrolo[2,1-f][1,2,4]triazin-7-yl)-4-fluoro-3-hydroxy-2-(hydroxymethyl)tetrahydrofuran-2-carbonitrile |
| 5 (EV0909) | 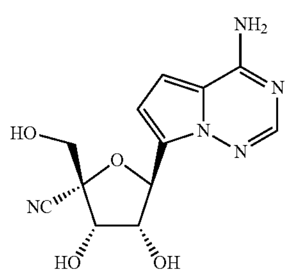 [SMILES: N#C[C@]1(CO)O[C@@H](c2ccc3c(N)ncnn23)[C@H](O)[C@@H]1O] | (2R,3S,4R,5S)-5-(4-aminopyrrolo[2,1-f][1,2,4]triazin-7-yl)-3,4-dihydroxy-2-(hydroxymethyl)tetrahydrofuran-2-carbonitrile |
| 6 (EV2290) | 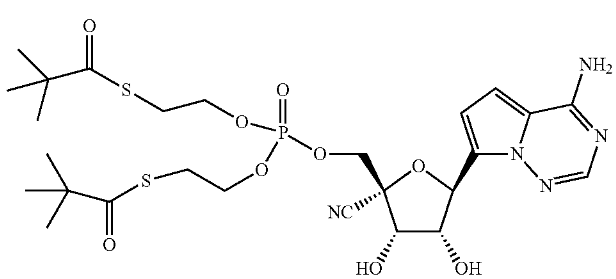 [SMILES: CC(C)(C)C(=O)SCCOP(=O)(OCCSC(=O)C(C)(C)C)OC[C@@]1(C#N)O[C@@H](c2ccc3c(N)ncnn23)[C@H](O)[C@@H]1O] | ((((2R,3S,4R,5R)-5-(4-aminopyrrolo[2,1-f][1,2,4]triazin-7-yl)-2-cyano-3,4-dihydroxytetrahydrofuran-2-yl)methoxy)(S,S'-(((hydroxyphosphoryl)bis(oxy))bis(ethane-2,1-diyl)) bis(2,2-dimethylpropanethioate)) |

-continued

| COMPOUND NO. | STRUCTURE | NAME |
|---|---|---|
| 7 (EV2242) | 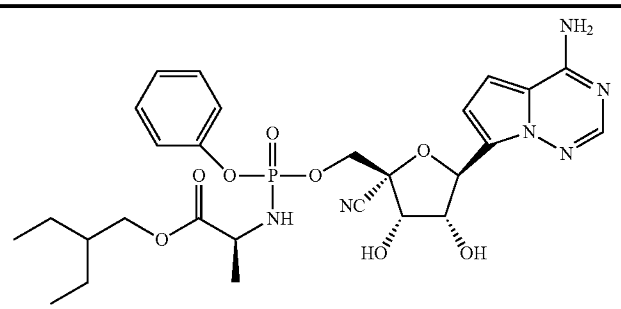 | 2-ethylbutyl ((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate |
| 8 (EV2259) | 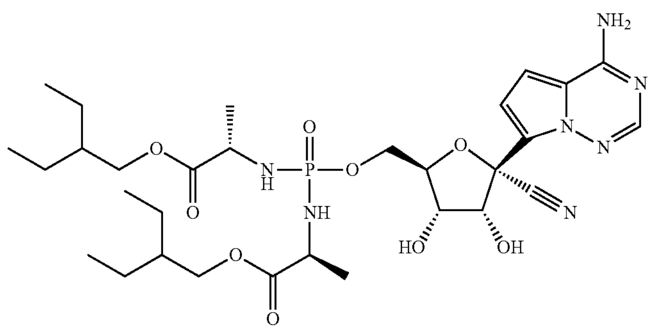 [SMILES: CCC(CC)COC(=O)[C@H](C)NP(=O)(N[C@@H](C)C(=O)OCC(CC)CC)OC[C@H]1O[C@@](C#N)(c2ccc3c(N)ncnn23)[C@H](O)[C@@H]1O] | ((2R,3S,4R,5R)-5-(4-aminopyrrolo[2,1-f][1,2,4]triazin-7-yl)-5-cyano-3,4-dihydroxytetrahydrofuran-2-yl)methyl phosphorodiamidate bis (2-ethylbutyl-L-alaninate) |
| 9 (EV2263) | 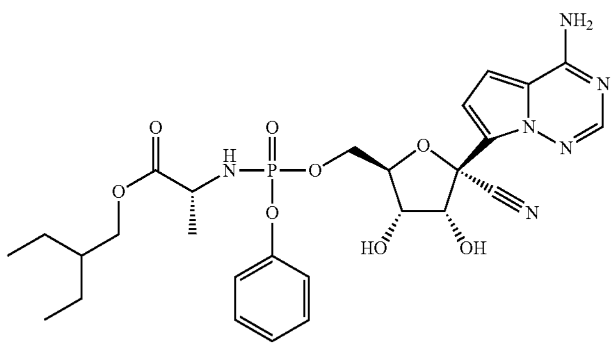 [SMILES: CCC(CC)COC(=O)[C@@H](C)NP(=O)(OC[C@H]1O[C@@](C#N)(c2ccc3c(N)ncnn23)[C@H](O)[C@@H]1O)Oc1ccccc1] | 2-ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-D-alaninate |

In some embodiments, the compound useful in the methods of the present invention is:

(2R,3R,4S,5R)-2-(4-aminopyrrolo[2,1-f][1,2,4]triazin-7-yl)-3,4-dihydroxy-5-(hydroxymethyl) tetrahydrofuran-2-carbonitrile The compound name provided above is named using ChemBioDraw Ultra and one skilled in the art understands that the compound structure may be named or identified using other commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, Compound 1:

Compound 1

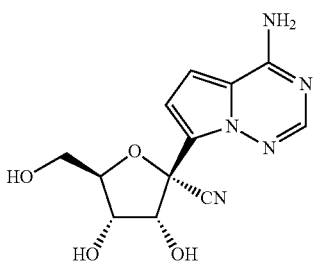

may be named or identified as (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile under IUPAC.

In some embodiments, the compound useful in the methods of the present invention is Compound 2.

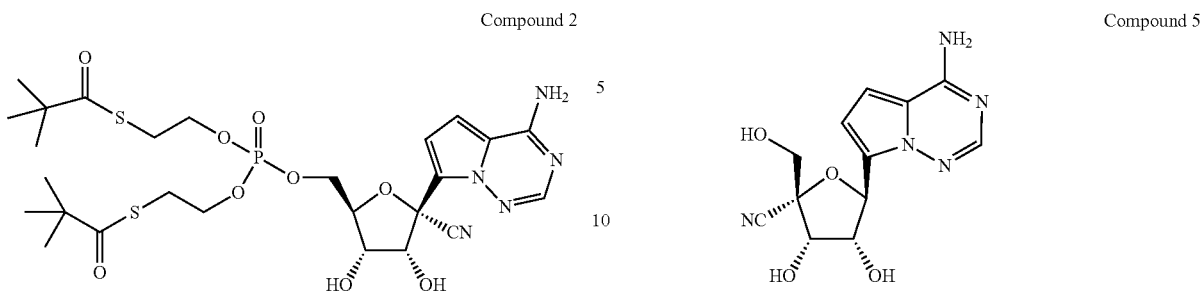

Compound 2

Compound 2 may be named or identified as (((((2R,3S,4R,5R)-5-(4-aminopyrrolo[2,1-f][1,2,4]triazin-7-yl)-5-cyano-3,4-dihydroxytetrahydrofuran-2-yl)methoxy) (S,S'-(((hydroxyphosphoryl) bis(oxy))bis(ethane-2,1-diyl))bis(2,2-dimethylpropanethioate)).

In some embodiments, the compound useful in the methods of the present invention is Compound 3:

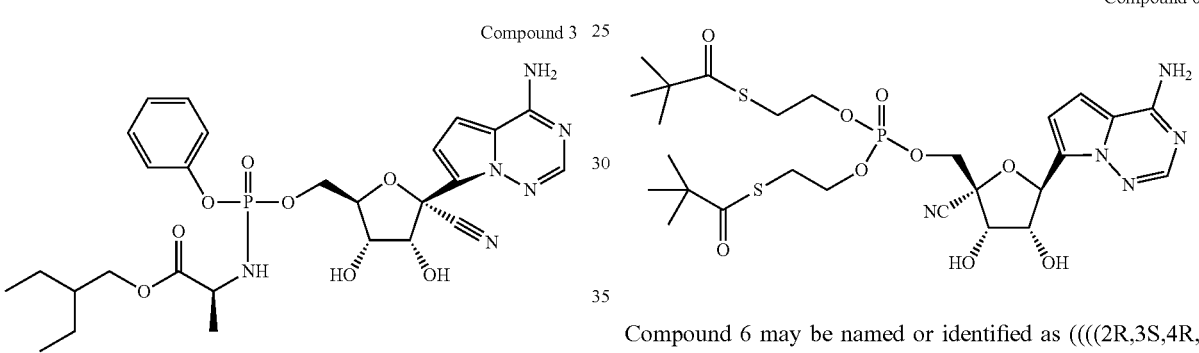

Compound 3

Compound 3 may be named or identified as 2-ethylbutyl (((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate under IUPAC.

In some embodiments, the compound useful in the methods of the present invention is Compound 4:

Compound 4

Compound 4 may be named or identified as (2R,3R,4R,5S)-5-(4-aminopyrrolo[2,1-f][1,2,4]triazin-7-yl)-4-fluoro-3-hydroxy-2-(hydroxymethyl)tetrahydrofuran-2-carbonitrile under IUPAC.

In some embodiments, the compound useful in the methods of the present invention is Compound 5:

Compound 5

Compound 5 may be named or identified as (2R,3S,4R,5S)-5-(4-aminopyrrolo[2,1-f][1,2,4]triazin-7-yl)-3,4-dihydroxy-2-(hydroxymethyl)tetrahydrofuran-2-carbonitrile under IUPAC.

In some embodiments, the compound useful in the methods of the present invention is Compound 6:

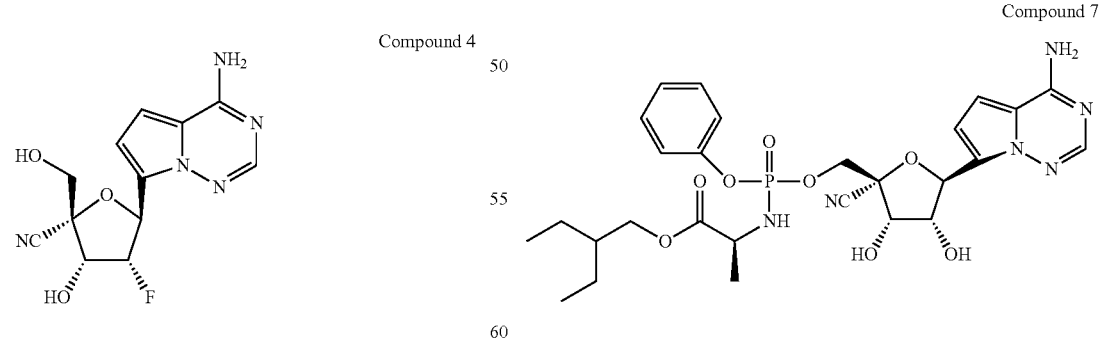

Compound 6

Compound 6 may be named or identified as (((((2R,3S,4R,5R)-5-(4-aminopyrrolo[2,1-f][1,2,4]triazin-7-yl)-2-cyano-3,4-dihydroxytetrahydrofuran-2-yl)methoxy)(S,S'-(((hydroxyphosphoryl)bis(oxy))bis(ethane-2,1-diyl))bis(2,2-dimethylpropanethioate)).

In some embodiments, the compound useful in the methods of the present invention is Compound 7:

Compound 7

Compound 7 may be named or identified as 2-ethylbutyl (((((2R,3S,4R,5S)-5-(4-aminopyrrolo[2,1-f][1,2,4]triazin-7-yl)-2-cyano-3,4-dihydroxytetrahydrofuran-2-yl)methoxy)(phenoxy)phosphoryl)-L-alaninate under IUPAC.

In some embodiments, the compound useful in the methods of the present invention is Compound 8:

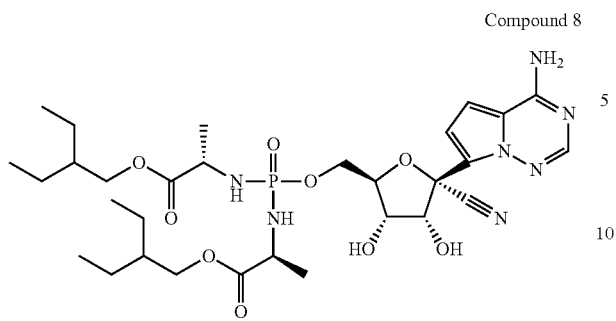

Compound 8

Compound 8 may be named or identified as ((2R,3S,4R,5R)-5-(4-aminopyrrolo[2,1-f][1,2,4]triazin-7-yl)-5-cyano-3,4-dihydroxytetrahydrofuran-2-yl)methyl phosphorodiamidate bis (2-ethylbutyl-L-alaninate).

In some embodiments, the compound useful in the methods of the present invention is Compound 9:

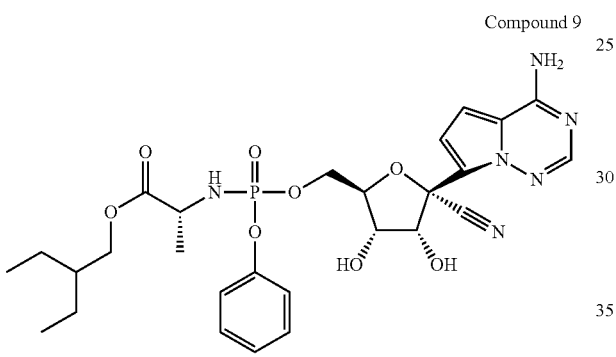

Compound 9

Compound 9 may be named or identified as 2-ethylbutyl ((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-D-alaninate under IUPAC.

B. Methods

The present invention provides a method of treating a feline Coronavirus infection comprising administering a therapeutically effective amount of a compound of Compound 1 to Compound 9, or a pharmaceutically acceptable salt thereof.

Pharmacokinetic evidence demonstrates that cats have a different drug metabolism profile than other species such as dogs or humans. For example, cats have slower rate of drug elimination due to the absence, or reduced expression, of many drug conjugating enzymes including those involved in glucuronidation (CYP), methylation (TPMT), and acetylation (NAT1 and NAT2). As a result, human drug metabolism and elimination is poorly correlated with what is observed in cats (*Vet Clin Small Anim* 2013, 43, 1039-1054).

In some embodiments, the present invention provides a method of treating a feline Coronavirus infection comprising administering a therapeutically effective amount of a compound:

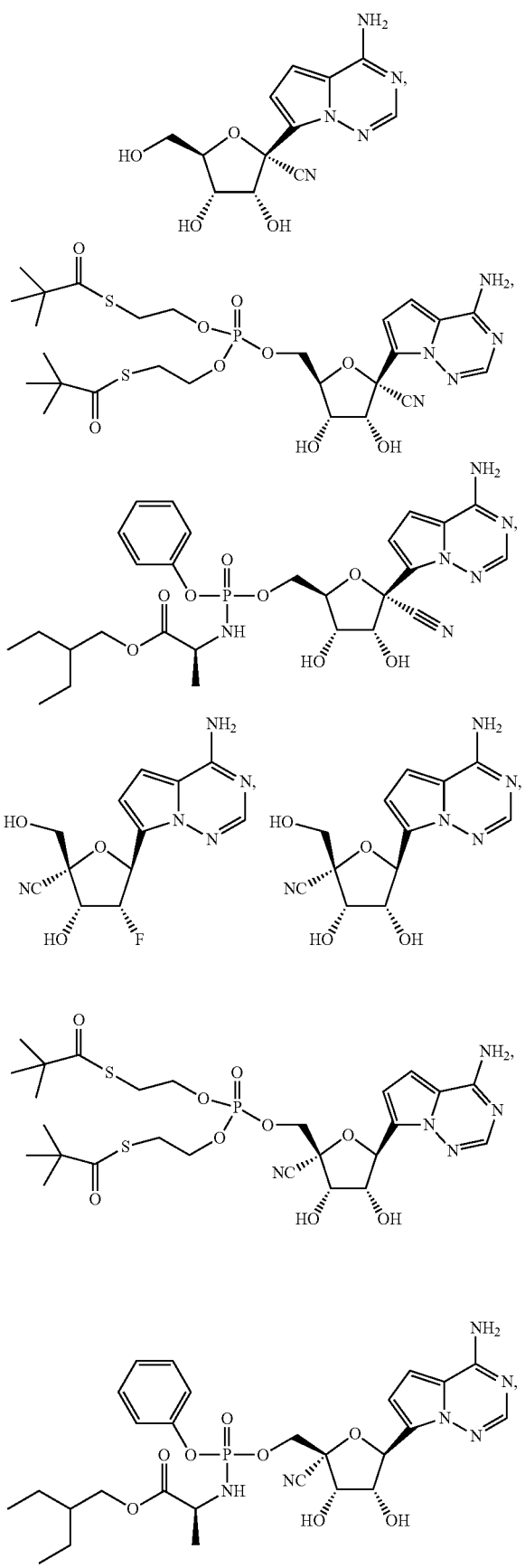

-continued

[chemical structure]

or a pharmaceutically acceptable salt thereof.

Provided is a method of treating a feline Coronavirus infection comprising administering a therapeutically effective amount of

[chemical structure]

or a pharmaceutically acceptable salt thereof.

In some embodiments, the Coronavirus is feline enteric coronavirus (FECV) or feline infectious peritonitis virus (FIPV).

Provided is a method of treating a feline Coronavirus infection comprising administering a therapeutically effective amount of

[chemical structure]

or a pharmaceutically acceptable salt thereof.

In some embodiments, the Coronavirus is feline enteric coronavirus (FECV) or feline infectious peritonitis virus (FIPV).

In some embodiments, the present invention provides a method of treating a feline enteric coronavirus (FECV) infection comprising administering a therapeutically effective amount of a compound:

[chemical structures]

17

-continued

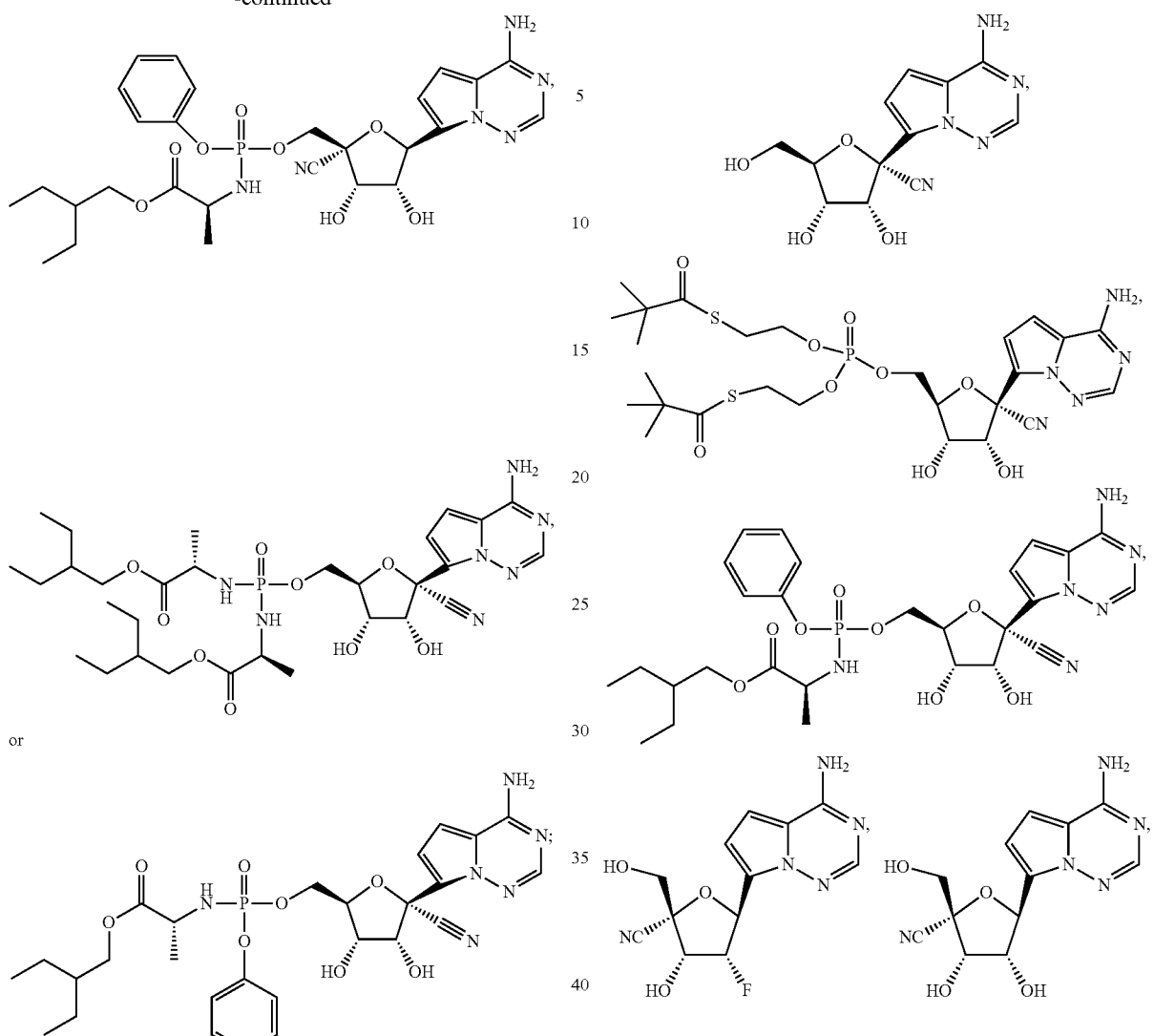

or a pharmaceutically acceptable salt thereof.

In some embodiments, a method of treating a feline enteric coronavirus (FECV) infection comprising administering a therapeutically effective amount of or a pharmaceutically acceptable salt thereof.

In some embodiments, the present invention provides a method of treating an infectious peritonitis virus (FIPV) infection comprising administering a therapeutically effective amount of a compound:

18

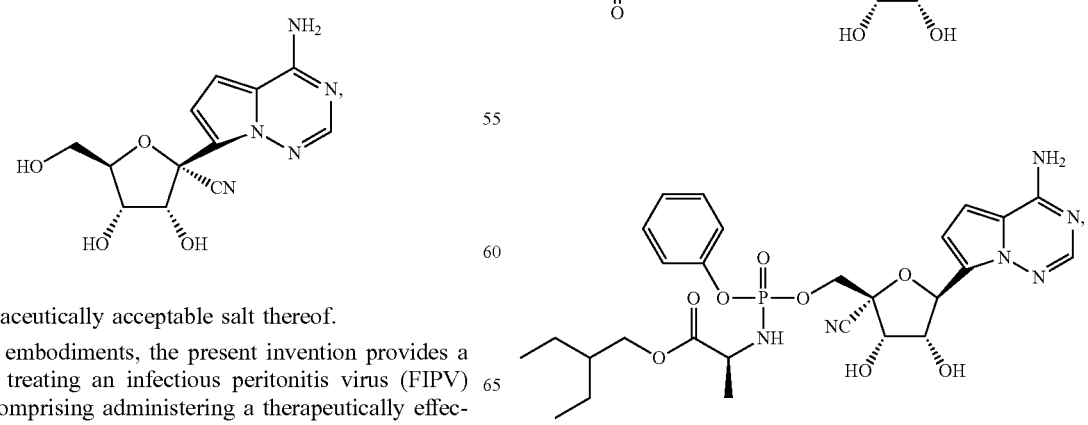

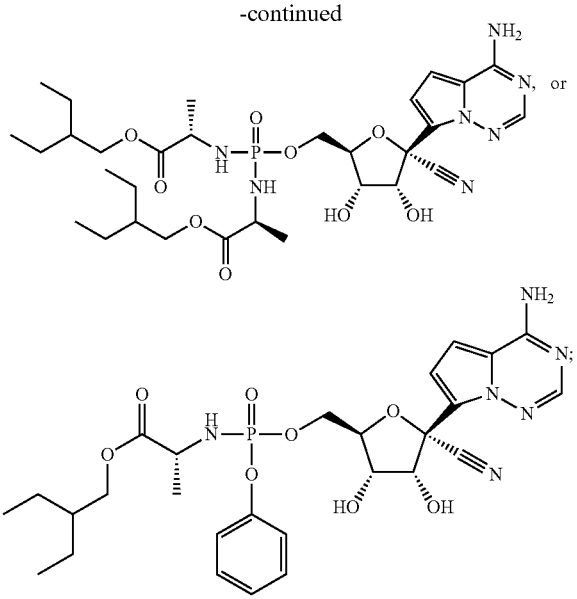

or a pharmaceutically acceptable salt thereof.

In some embodiments, a method of treating an infectious peritonitis virus (FIPV) infection comprising administering a therapeutically effective amount of or a pharmaceutically acceptable salt thereof.

In some embodiments, the present invention provides a method of treating feline infectious peritonitis (FIP) comprising administering a therapeutically effective amount of a compound:

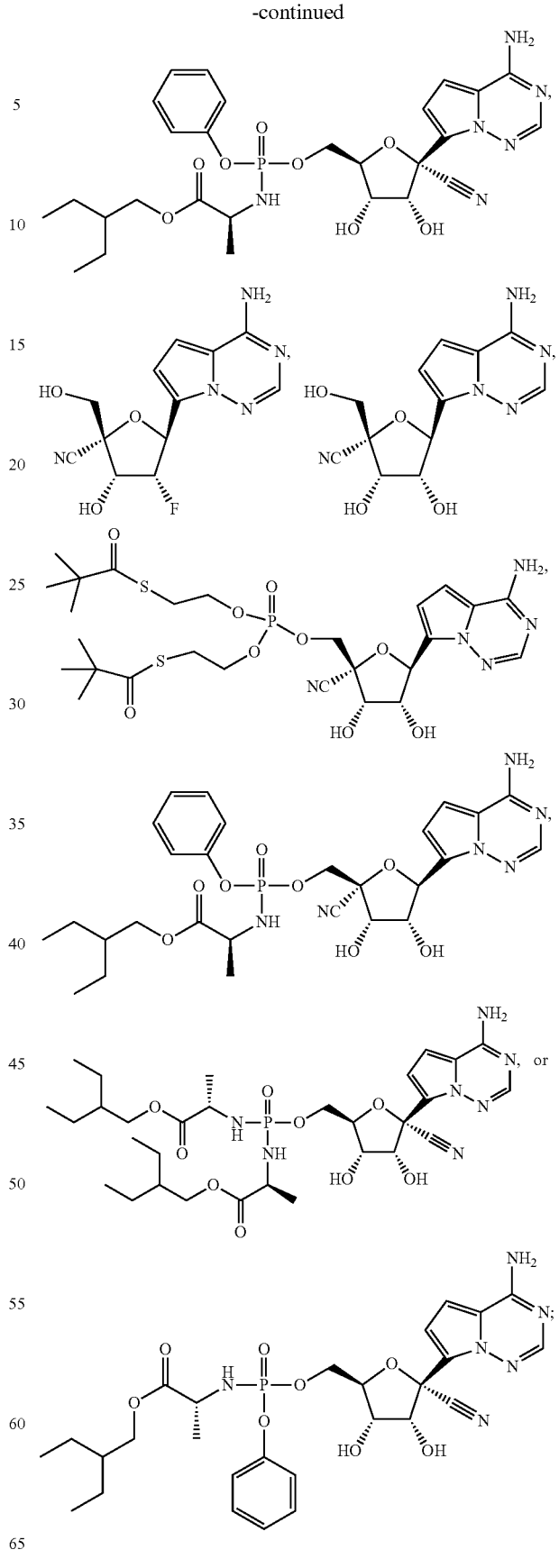

or a pharmaceutically acceptable salt thereof.

In some embodiments, a method of treating feline infectious peritonitis (FIP) comprising administering a therapeutically effective amount of

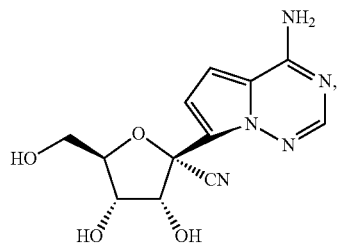 [SMILES: N#C[C@@]1(c2ccc3c(N)ncnn23)O[C@H](CO)[C@@H](O)[C@H]1O]

or a pharmaceutically acceptable salt thereof.

The compounds of the present invention can be prepared by methods known to one of skill in the art. For example, the compounds of the present invention can be prepared according to the methods described in U.S. Pat. Nos. 8,008,264, and 7,973,013, and PCT Publication Nos. WO2012/012776 and WO 2015/069939.

III. Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10. In some embodiments, the pH of the formulations ranges from about 2 to about 5, but is ordinarily about 3 to 4.

While it is possible for the active ingredients to be administered alone it may be preferable to present them as pharmaceutical formulations. The formulations for veterinary may comprise at least one active ingredient, as above defined, together with one or more acceptable carriers therefor and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate. Further emulgents and emulsion stabilizers suitable for use in the formulation of the invention include Tween® 80.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Further non-limiting examples of suspending agents include Cyclodextrin and Captisol (=Sulfobutyl ether beta-cyclodextrin; SEB-beta-CD).

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, and hypertonic sodium chloride solution.

The amount of active ingredient that may be combined with the carrier material to produce a single dosage form will vary depending upon the host treated and the particular mode of administration. For example, a time-release formulation intended for oral administration to feline may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Coronavirus infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

IV. Routes of Administration

One or more compounds of the invention (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient.

In the methods of the present invention for the treatment of Coronavirus infections, the compounds of the present invention may be administered at any time to a feline who may come into contact with other felines suffering from Coronavirus infections or is already suffering from Coronavirus infection. In some embodiments, the compounds of the present invention can be administered prophylactically to felines coming into contact with other felines suffering from Coronavirus infection. In some embodiments, administration of the compounds of the present invention can be to felines testing positive for Coronavirus infection but not yet showing symptoms of Coronavirus infection. In some embodiments, administration of the compounds of the present invention can be to felines upon commencement of symptoms of Coronavirus infection.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day.

The effective dose of a compound of the present invention for treating the Coronavirus infection can depend on whether the dose is to be used prophylactically or to treat a feline already suffering from Coronavirus infection. Moreover, the dose can depend on whether the feline suffering from Coronavirus infection does not yet show symptoms or is already showing symptoms of Coronavirus infection. Larger doses may be necessary for treating felines testing positive for Coronavirus infection and for felines showing symptoms of Coronavirus infection as compared to felines receiving prophylactic treatment.

Any suitable period of time for administration of the compounds of the present invention is contemplated. For example, administration can be for from 1 day to 100 days, including 2, 3, 4, 5, 6, 7, 8, 9, 10, 15, 20, 25, 30, 40, 50, 60, 70, 80, or 90 days. The administration can also be for from 1 week to 15 weeks, including 2, 3, 4, 5, 6, 7, 8, 9, 10, 11, 12, 13, or 14 weeks. Longer periods of administration are also contemplated. The time for administration can depend on whether the compound is being administered prophylactically or to treat a feline suffering from a Coronavirus infection. For example, a prophylactic administration can be for a period of time while the feline is in regular contact with other felines suffering from a Coronavirus infection, and for a suitable period of time following the last contact with a feline suffering from a Coronavirus infection. For felines already suffering from a Coronavirus infection, the period of administration can be for any length of time necessary to treat the animal and a suitable period of time following a negative test for Coronavirus infection to ensure the Coronavirus infection does not return.

V. Examples

Example 1. Treating Feline Coronavirus

Compound 1 was screened for activity against feline Coronaviruses in an in vitro assay. Serial dilutions of Compound 1 were mixed with $2.5 \times 10^4$ copies of feline coronavirus and added in sextuplicate to 96 well plates with pre-seeded CRFK cells. The plates were incubated for 72 hours followed by a staining of the cell culture monolayers with crystal violet. The level of virus-induced cytopathic effect was quantified visually and using a plate reader. Positive control wells comprised the virus without Compound 1. Negative control wells lacked both virus and Compound 1. The $EC_{50}$ was calculated by regression analysis. The $EC_{50}$ of Compound 1 is shown in Table 1.

TABLE 1

|  | $EC_{50}$ |
| --- | --- |
| Compound 1 | 0.77 µM |

Compound 1 was screened for cytotoxicity in uninfected CRFK cells using a commercially available CellTox Green Cytotoxicity Assay (Promega). The assayed was performed in a 96 well place formate using serial dilution of Compound 1 in sextuplicate. Compound concentration associated with 50% cytotoxicity ($CC_{50}$) following 72 hour incubation was calculated by regression analysis. The $CC_{50}$ of Compound 1 is shown in Table 2. See FIG. 1.

TABLE 2

|  | $CC_{50}$ |
| --- | --- |
| Compound 1 | >100 µM |

Example 2. Treatment Assay

Compounds were tested for antiviral activity against feline infectious peritoneal virus (FIPV) in Crandell Rees Feline Kidney (CRFK) cells. Serial dilution of compounds were mixed 10 to 100 TCID50 of FIPV and added to 96-well plates containing pre-seeded CRFK cells. The plates were incubated for 48 hours at 37° C. After the incubation, the CRFK cell monolayer was stained using crystal violet and the level of FIPV-induced cytopathic effect was quantified using an absorbance plate reader. $EC_{50}$ values were determined using nonlinear regression analysis. See FIG. 1 to FIG. 15.

All publications, patents, and patent documents cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A method of treating a feline Coronavirus infection in a cat in need thereof comprising administering to the cat a therapeutically effective amount of a compound of formula:

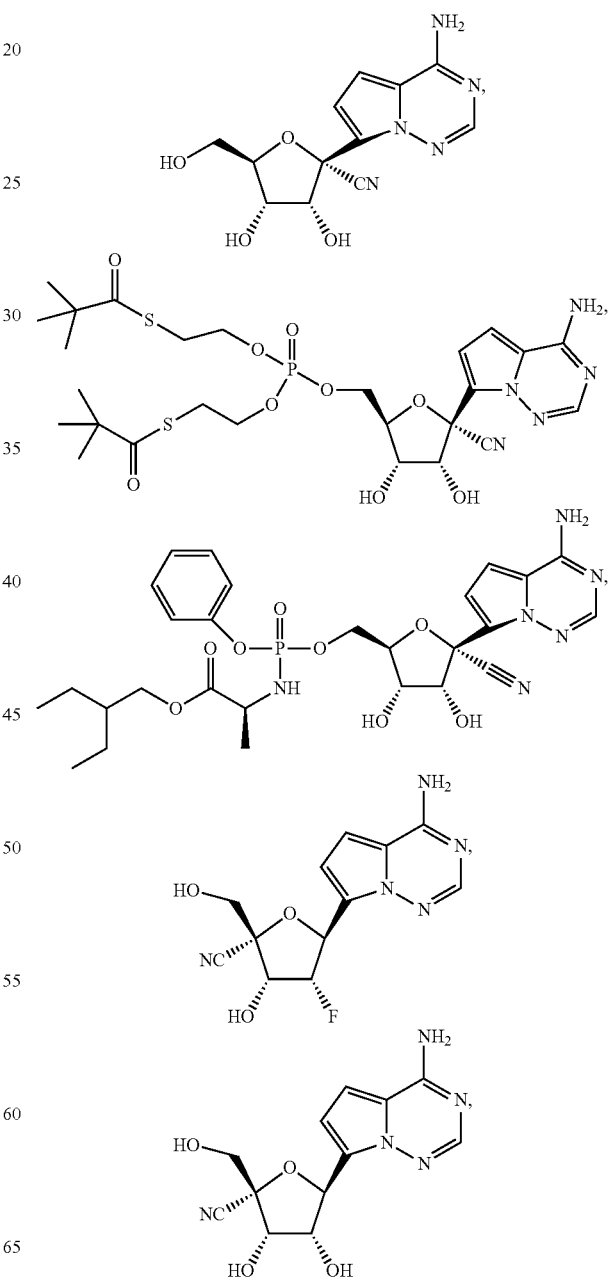

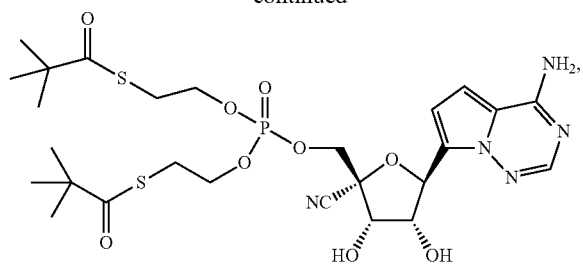

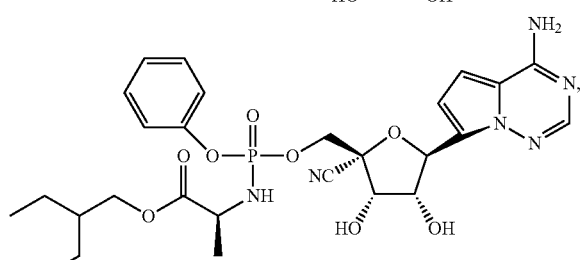

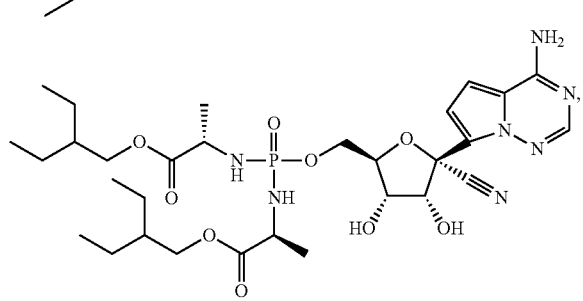

or

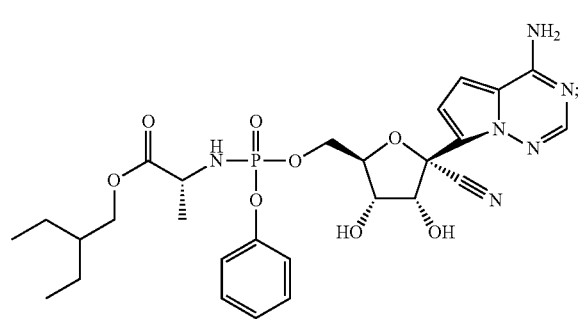

or a pharmaceutically acceptable salt thereof.

2. The method of claim 1, wherein the feline Coronavirus infection is feline enteric coronavirus (FECV) or feline infectious peritonitis virus (FIPV).

3. The method of claim 1, wherein the compound is a compound of formula:

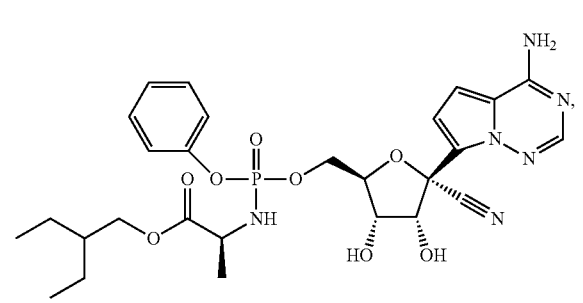

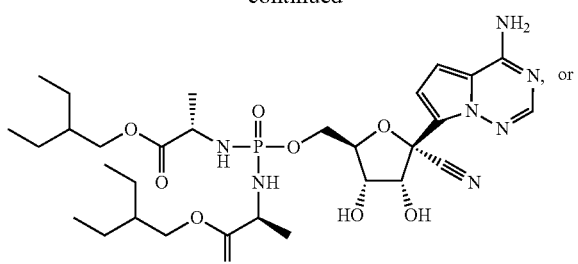

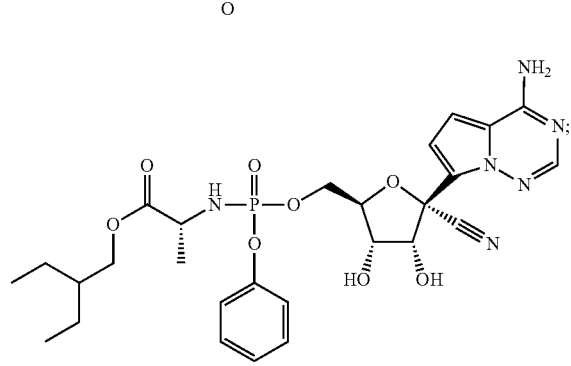

or a pharmaceutically acceptable salt thereof.

4. A method of treating a feline Coronavirus infection in a cat in need thereof comprising administering to the cat a therapeutically effective amount of a compound of formula

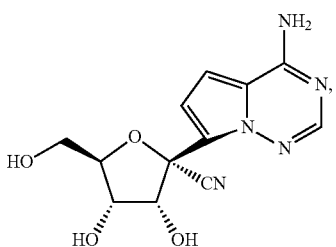 [SMILES: N#C[C@@]1(c2ccc3c(N)ncnn23)O[C@H](CO)[C@@H](O)[C@H]1O]

or a pharmaceutically acceptable salt thereof.

5. The method of claim 4, wherein the feline Coronavirus infection is feline enteric coronavirus (FECV) or feline infectious peritonitis virus (FIPV).

6. The method of claim 4, wherein the compound is a compound of formula:

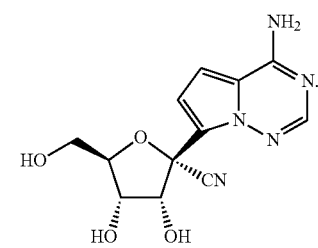

7. A method of treating a feline enteric coronavirus (FECV) infection in a cat in need thereof comprising administering to the cat a therapeutically effective amount of a compound of formula:

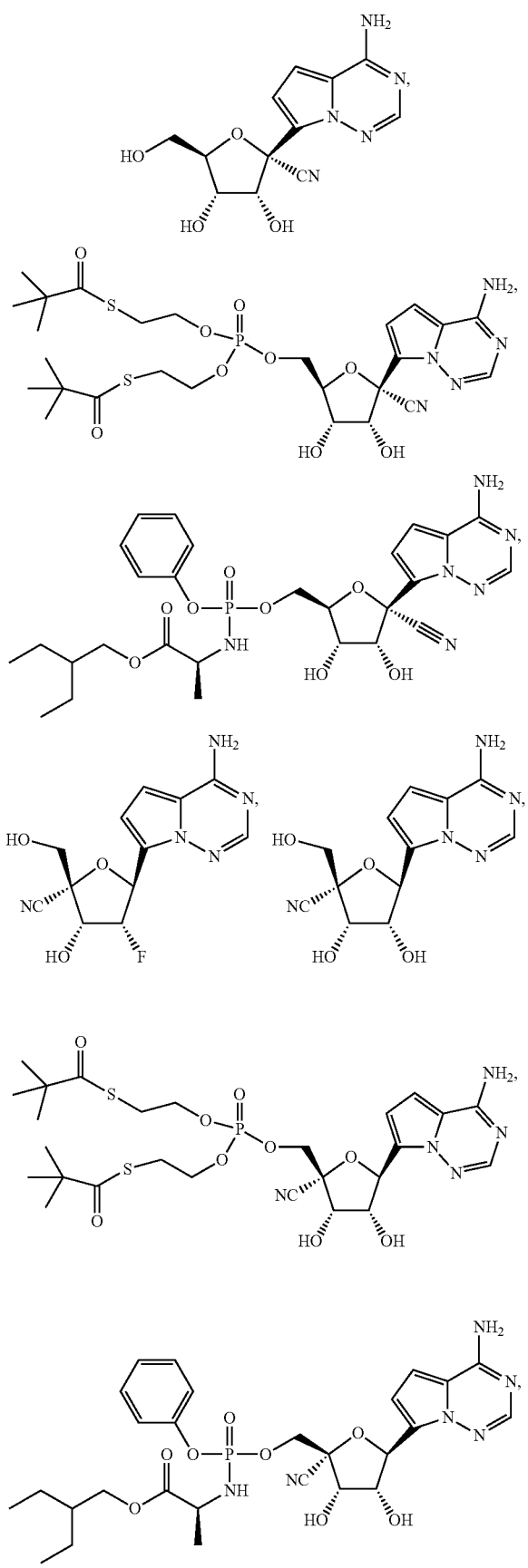
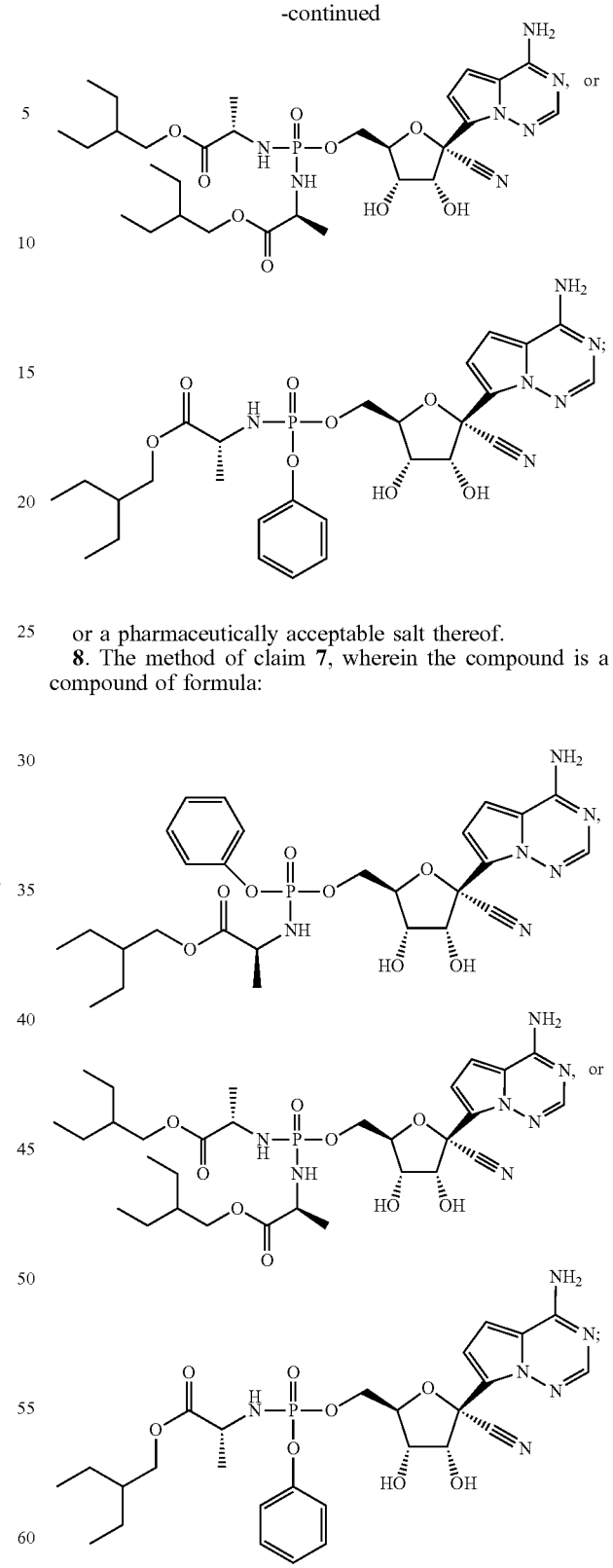
or a pharmaceutically acceptable salt thereof.
8. The method of claim 7, wherein the compound is a compound of formula:
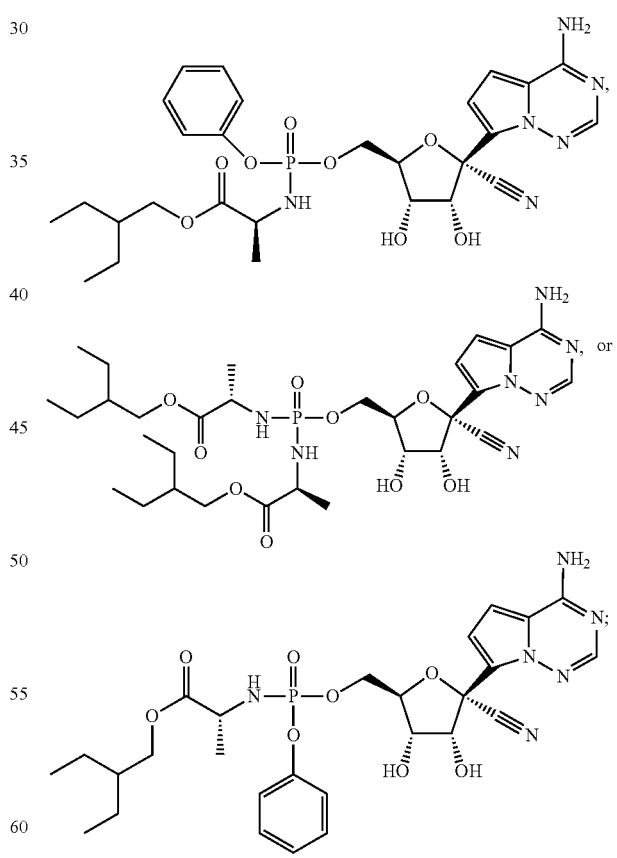
or a pharmaceutically acceptable salt thereof.
9. A method of treating a feline enteric coronavirus (FECV) infection in a cat in need thereof comprising administering to the cat a therapeutically effective amount of a compound of formula

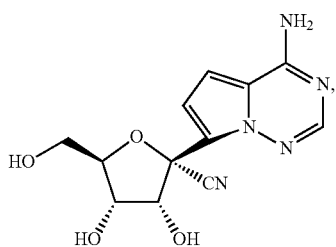 [SMILES: N#C[C@@]1(c2ccc3c(N)ncnn23)O[C@H](CO)[C@@H](O)[C@H]1O]

or a pharmaceutically acceptable salt thereof.

10. The method of claim 9, wherein the compound is a compound of formula:

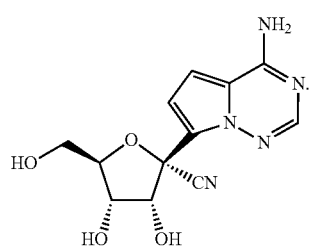 [SMILES: N#C[C@@]1(c2ccc3c(N)ncnn23)O[C@H](CO)[C@@H](O)[C@H]1O]

11. A method of treating a feline infectious peritonitis virus (FIPV) infection in a cat in need thereof comprising administering to the cat a therapeutically effective amount of a compound of formula:

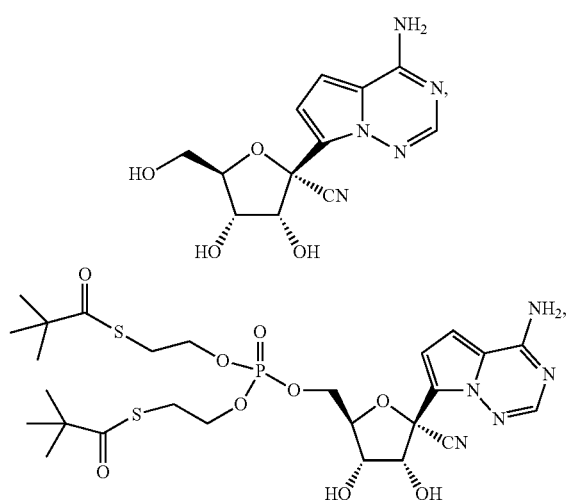

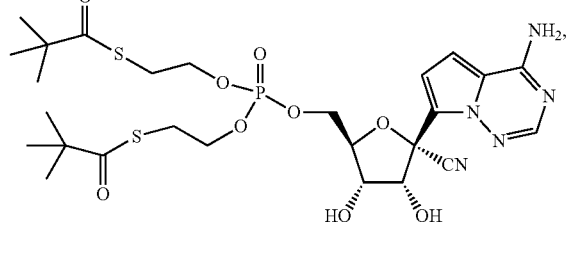

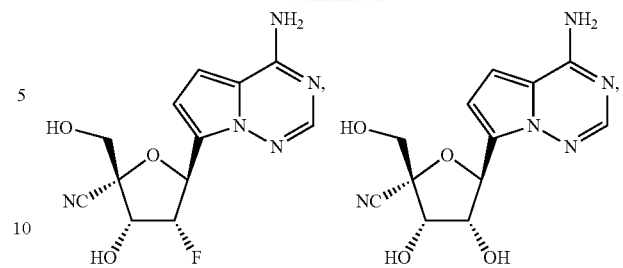

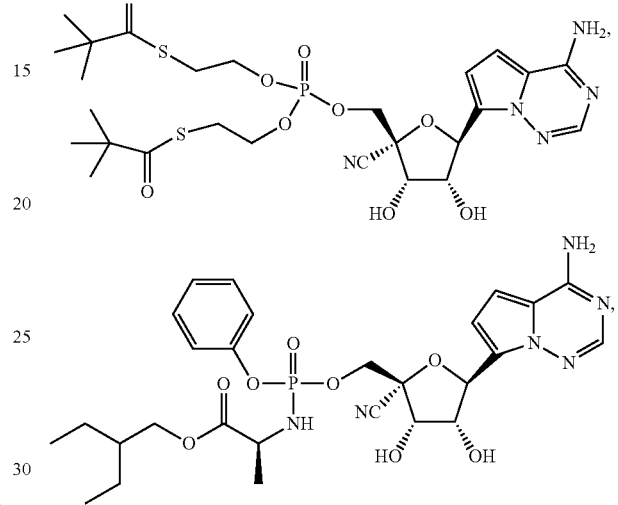

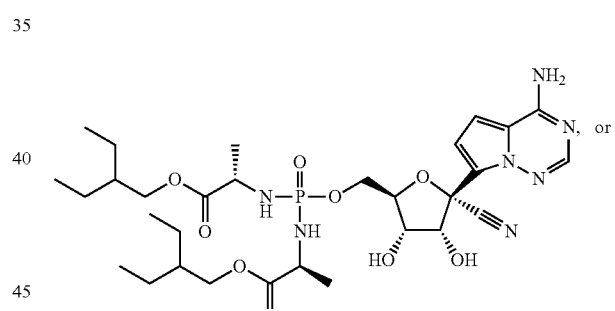

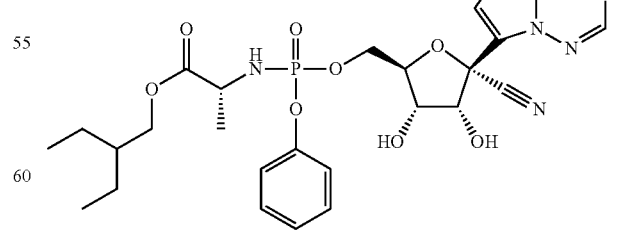

or a pharmaceutically acceptable salt thereof.

12. The method of claim 11, wherein the compound is a compound of formula:

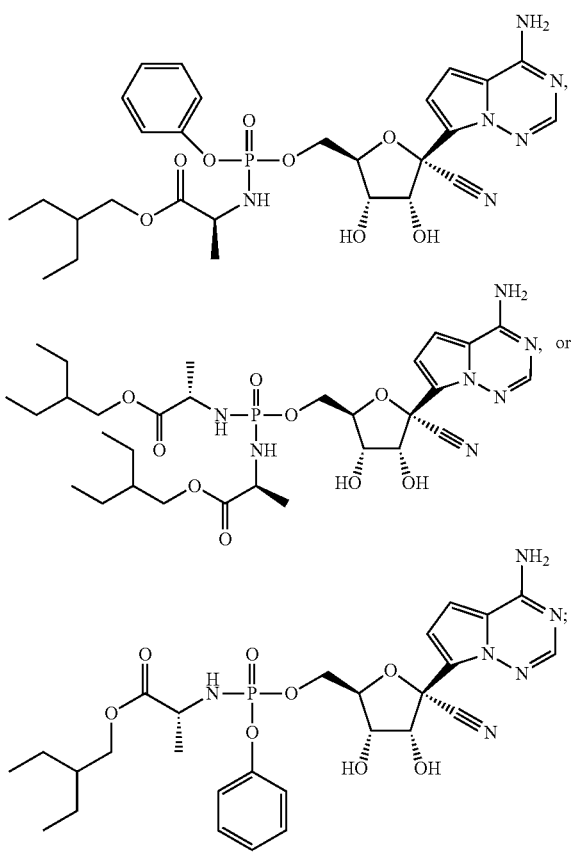

or a pharmaceutically acceptable salt thereof.

13. A method of treating feline infectious peritonitis virus (FIPV) infection in a cat in need thereof comprising administering to the cat a therapeutically effective amount of a compound of formula

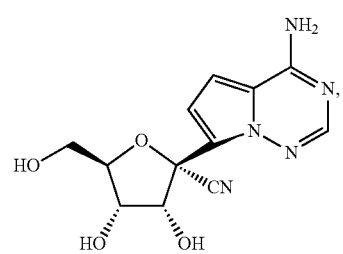 [SMILES: N#C[C@@]1(c2ccc3c(N)ncnn23)O[C@H](CO)[C@@H](O)[C@H]1O]

or a pharmaceutically acceptable salt thereof.

14. The method of claim 13, wherein the compound is a compound of formula:

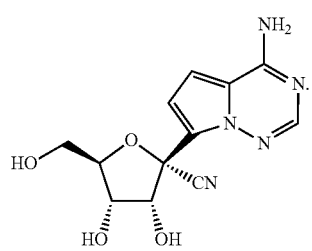 [SMILES: N#C[C@@]1(c2ccc3c(N)ncnn23)O[C@H](CO)[C@@H](O)[C@H]1O]

15. A method of treating feline infectious peritonitis (FIP) in a cat in need thereof comprising administering to the cat a therapeutically effective amount of a compound of formula:

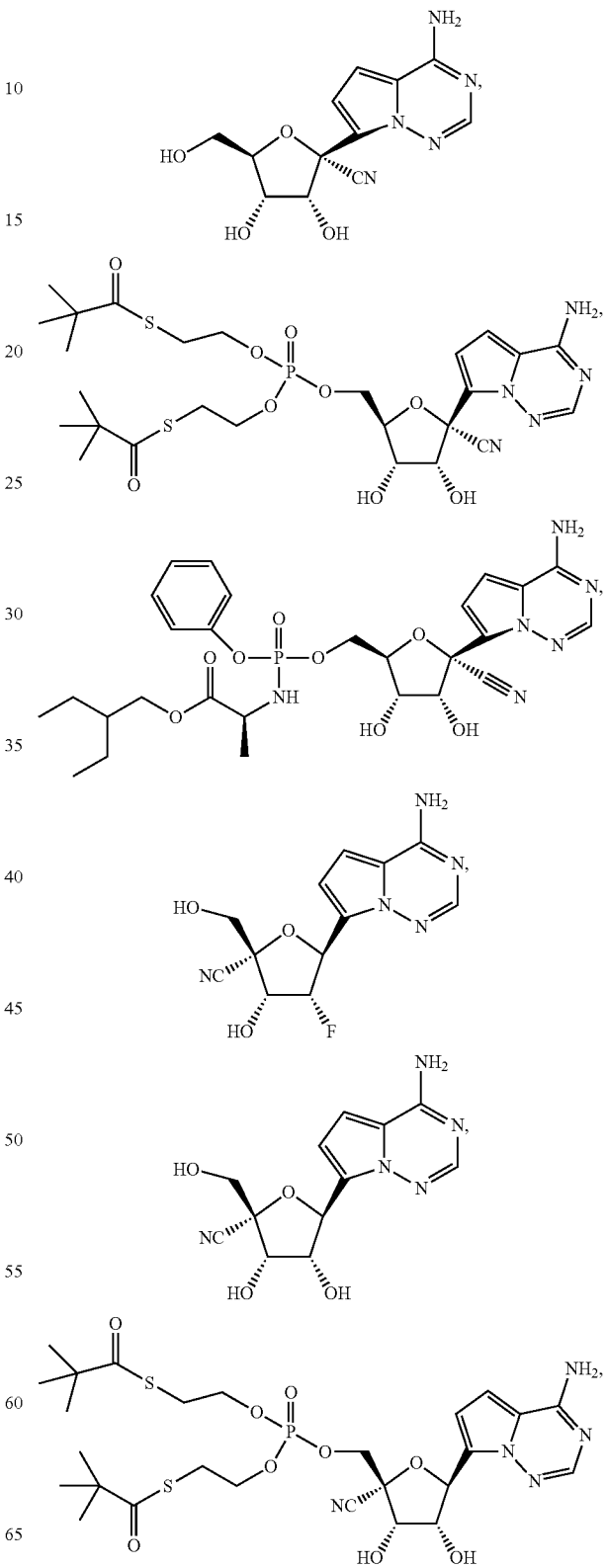

-continued

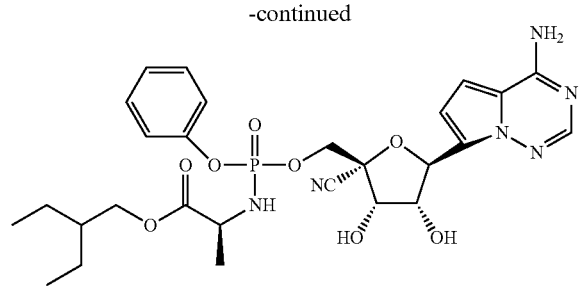

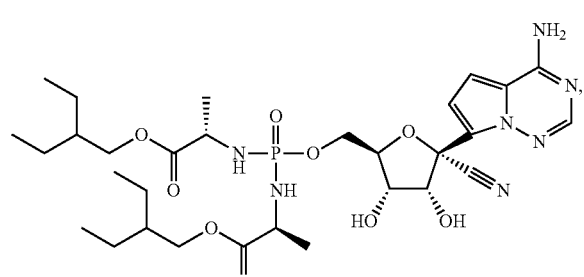

or

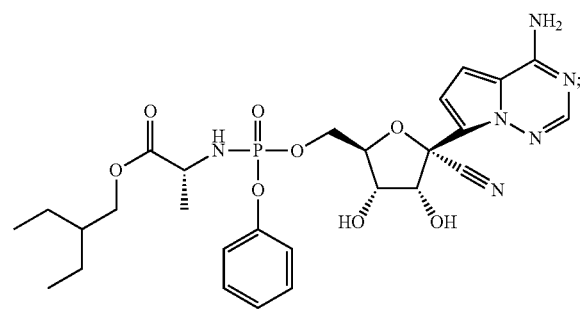

or a pharmaceutically acceptable salt thereof.
16. The method of claim 15, wherein the compound is a compound of formula:

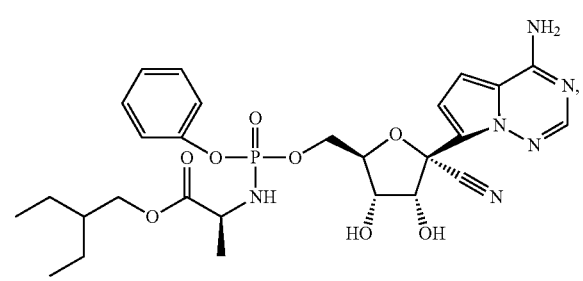

-continued

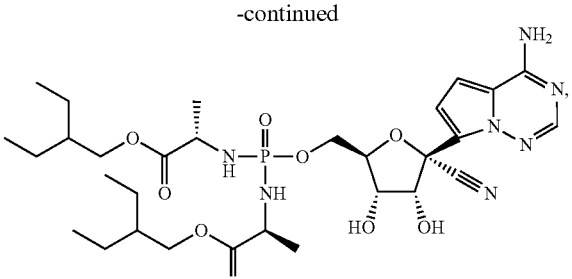

or

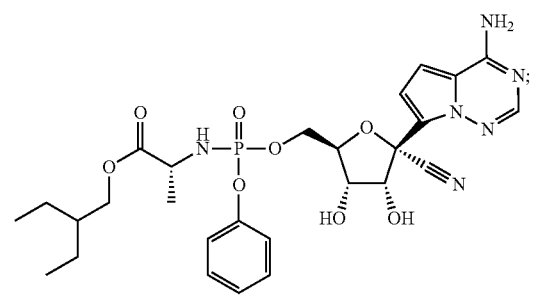

or a pharmaceutically acceptable salt thereof.
17. A method of treating feline infectious peritonitis (FIP) in a cat in need thereof comprising administering to the cat a therapeutically effective amount of a compound of formula

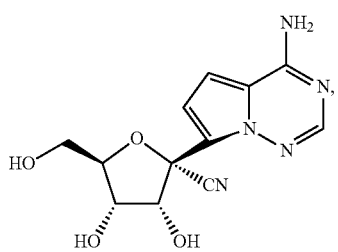

or a pharmaceutically acceptable salt thereof.
18. The method of claim 17, wherein the compound is a compound of formula:

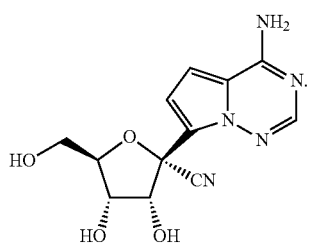 [SMILES: N#C[C@@]1(c2ccc3c(N)ncnn23)O[C@H](CO)[C@@H](O)[C@H]1O]

* * * * *